United States Patent [19] [11] 4,199,481
Hall et al. [45] Apr. 22, 1980

[54] ACETYLATED ALPHA METHYL STYRENE DIMERS OR DERIVATIVES IN PERFUMES

[75] Inventors: John B. Hall, Rumson; Wilhelmus J. Wiegers, Red Bank; Ira D. Hill, Locust; Robert M. Novak, Fords; Frederick L. Schmitt, Holmdel, all of N.J.

[73] Assignee: International Flavors & Fragrances Inc., New York, N.Y.

[21] Appl. No.: 46,551

[22] Filed: Jun. 7, 1979

[51] Int. Cl.$^2$ ............................ C11B 9/00; A61K 7/46
[52] U.S. Cl. ................................ 252/522 R; 585/406; 252/522 A
[58] Field of Search ...................... 252/522 R, 522 A; 585/406

[56] References Cited

U.S. PATENT DOCUMENTS

| | | | |
|---|---|---|---|
| 3,161,692 | 12/1964 | McLaughlin | 585/27 |
| 3,523,981 | 8/1970 | Ottmann et al. | 585/406 |
| 3,890,402 | 6/1975 | Stapp | 585/406 |
| 3,966,902 | 6/1976 | Chromecek | 252/522 A |
| 4,081,489 | 3/1978 | Bateman | 585/406 |
| 4,142,998 | 3/1979 | Hall et al. | 252/522 R |
| 4,165,301 | 8/1979 | Wiegers et al. | 252/522 R |

*Primary Examiner*—Veronica O'Keefe
*Attorney, Agent, or Firm*—Arthur L. Liberman; Franklin D. Wolffe

[57] ABSTRACT

A process is described for providing clear extended compositions of essential oils which comprises a composition of an essential oil and an extender material miscible with said essential oil which does not appreciably alter the aroma of the essential oil insofar as its quality or strength is concerned, the proportion of essential oil in extender material being from about 70% up to about 99%, said extender material being an acylated dimerization product of an alpha methyl styrene or a methyl or other $C_2$–$C_4$ lower alkyl homologue thereof or hydrogenated derivative thereof or mixture of same.

7 Claims, 10 Drawing Figures

GLC PROFILE FOR EXAMPLE I, FRACTION 19.

GLC PROFILE FOR EXAMPLE I, FRACTION 3.

MASS SPECTRUM FOR EXAMPLE I, FRACTION 3, AND EXAMPLE III.

GLC PROFILE FOR EXAMPLE III, FRACTIONS 9-12.

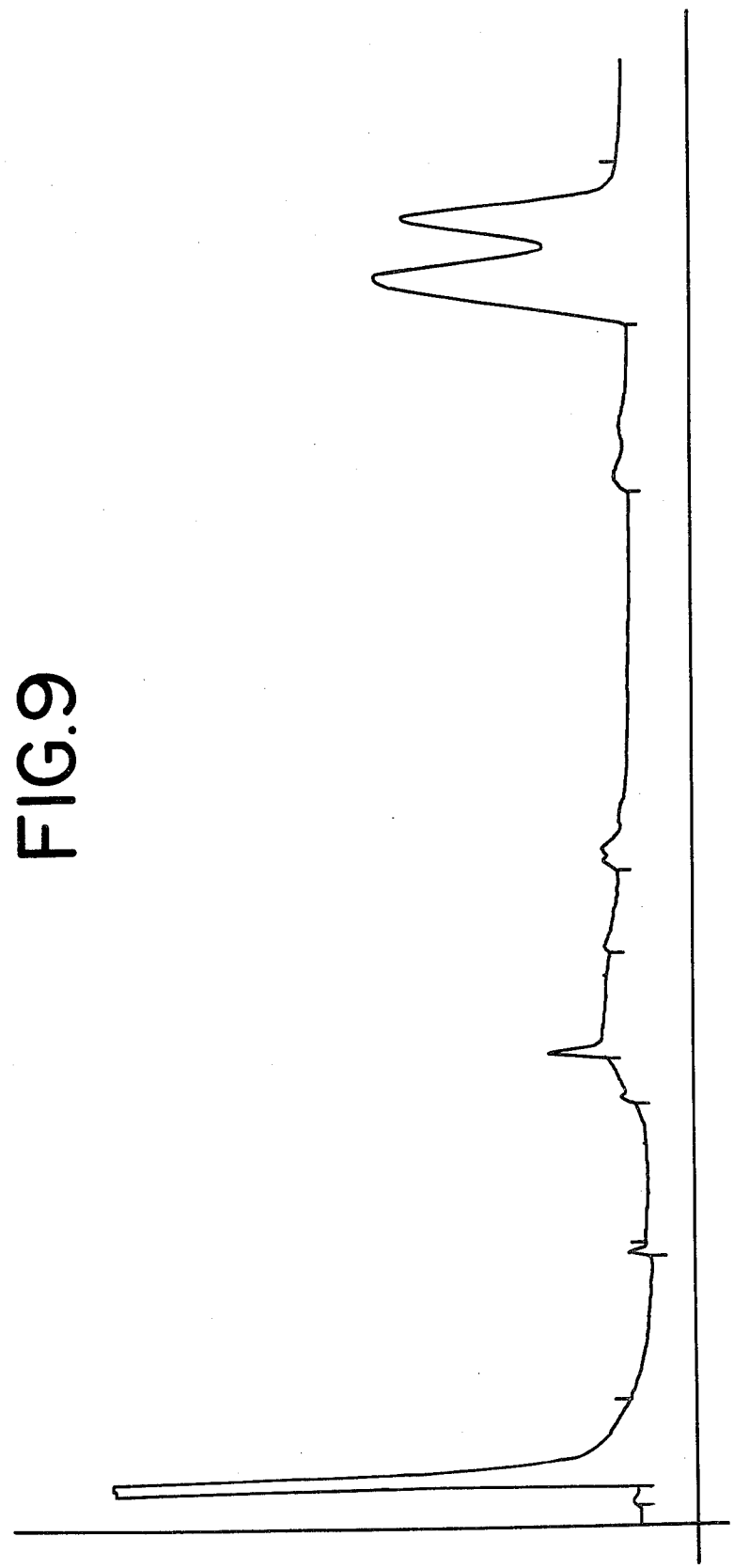

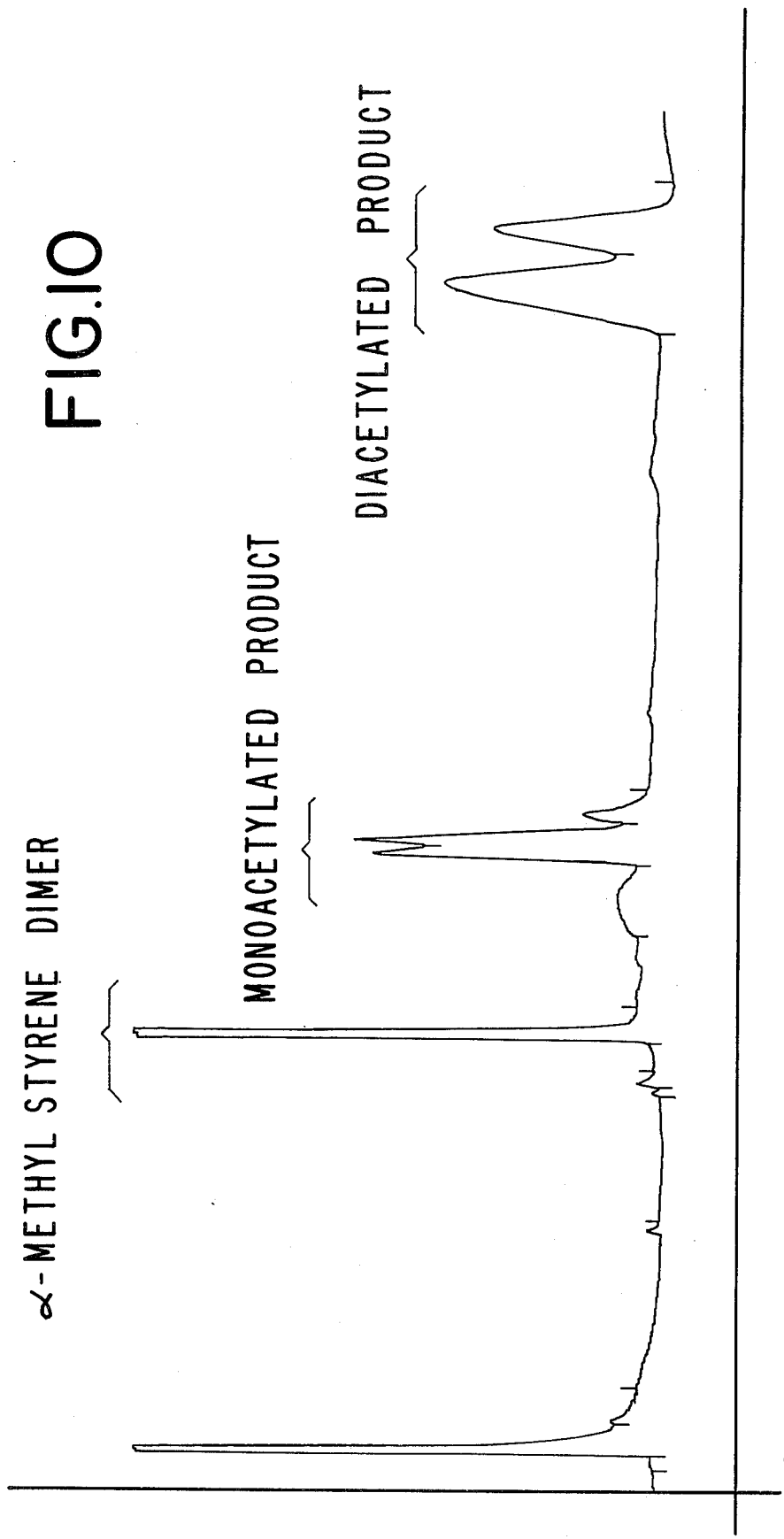

ACETYLATED ALPHA METHYL STYRENE DIMERS OR DERIVATIVES IN PERFUMES

BACKGROUND OF THE INVENTION

Compounded perfumery compositions contain a number of ingredients which may be of natural or synthetic origin. The ingredients are blended by the perfumer to create the desired odor effect. Such essential oils which contain high percentages of hydrocarbon constituents such as patchouli oil (an essential oil derived from Pogostemon Patchouli) have, for example, warm aromatic spicey odors. When the perfumer wishes to include this type of note for example in a perfumery composition of an oriental type, he will use patchouli oil. However, such natural oils as oil of patchouli are expensive essential oils and are of limited availability. Even more extreme examples are natural sandalwood oil and natural vetiver oil. Although, attempts have been made to simulate the odor of patchouli oil, sandalwood oil and vetiver oil by use of blends of synthetic perfumery chemicals, the creation of such oils having identical aromas with reference to the natural oils has not been achieved.

In U.S. Pat. No. 3,673,120 issued on June 27, 1972, 8-camphene carbinol was indicated to be useful as a perfumery extender for patchouli oil in perfumery compositions when present in a concentration of from 1 to 200 parts by weight per 100 parts by weight of the patchouli oil. However, 8-camphene carbinol has the disadvantage of significantly decreasing the aroma strength of the patchouli oil and is not versatile for use with oils other than patchouli oil, for example, vetiver oil and sandalwood oil in the genus of natural oils, and synthetic oils, for example, geranonitrile and cinnamonitrile.

In U.S. Pat. No. 2,422,145 issued on June 10, 1947, water-soluble hydroxy polyoxyethylene ethers of partial higher fatty acid esters of low molecular weight polyhydroxylic compounds were found to form clear extended solutions with essential oils which could be used as such or which would be diluted with water to form stable dispersions or solutions of essential oils. Specifically disclosed are compositions containing clear, stable solutions of a quantity of an essential oil and at least an equal quantity of such ethers as mannitan monopalmitate hydroxy polyoxyethylene ether with about 20 oxyethylene units per mole with such solution being capable, upon dilution with water, of forming a clear, stable aqueous dispersion of essential oil and hydroxy polyoxyethylene ether. U.S. Pat. No. 2,422,145, however, does not disclose the formation of solutions of essential oil in organic solvents which are immiscible with water. Furthermore, the ethers of U.S. Pat. No. 2,422,145 significantly reduce the strength of the perfumery material when used in conjunction with same.

Cyclohexane dicarboxylic acid diesters having the structure:

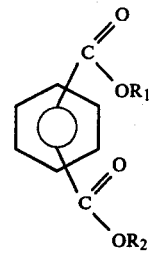

wherein $R_1$ and $R_2$ are less than 13 carbon aliphatic or alicyclic hydrocarbon moieties are disclosed to be useful "perfume harmonizing agents" in Japanese Published Application at J 52136927 issued on Nov. 15, 1977 to Asahi Denka Kogyo. However, such materials as these cyclohexane dicarboxylic acid diesters detract from the strength of the perfume material with which it is used.

Processes for preparing alpha methyl styrene dimers and methyl homologues thereof are broadly disclosed in the prior art, for example, French Pat. No. 1,317,412 assigned to Socony Mobil Oil Company dated Feb. 8, 1963;

U.S. Pat. No. 3,161,692 issued on Dec. 15, 1964 assigned to Socony Mobil Oil Company;

U.S.S.R. Pat. No. 191,511 issued on Jan. 26, 1967;

U.S. Pat. No. 3,523,981 assigned to Olin Corporation, issued on Aug. 11, 1970;

Deutsche Offenlengungschrift No. 2,101,089 issued on Aug. 10, 1972;

U.S. Pat. No. 3,890,402 assigned to Phillips Petroleum Company issued on June 17, 1975;

Petropoulos and Fisher, J.Am.Chem.Soc., 80, 1938–41 (1958); and

U.S. Pat. No. 4,081,489 issued on Mar. 28, 1978.

U.S. Pat. No. 4,081,489 disclosed an improved process for the production of compounds having the formula:

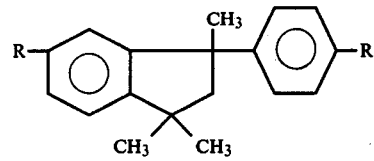

wherein R is independently hydrogen or methyl by contracting a compound of Formula I:

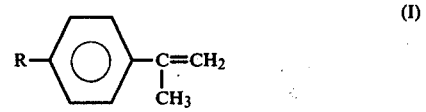

(I)

where mixture of compounds of Formula I, wherein R is hydrogen or methyl, with a sulfuric acid catalyst at a temperature of 100° to 225° C. which comprises a catalyst consisting essentially of about 0.05 up to about 3 weight percent based on the weight of the compound or mixture of compounds of Formula I, of 90 to 98% concentrated sulfuric acid.

Our U.S. Application for Letters Patent, Ser. No. 902,565 filed on May 3, 1978 (now U.S. Pat. No. 4,142,997 issued on Mar. 6, 1979) teaches the process for providing a clear extended composition of essential oils which comprises a composition of an essential oil and an extender material miscible with said essential oil which does not appreciably alter the aroma of the essential oil insofar as its quality or strength is concerned, the proportion of essential oil in extender material being a dimerization product of an alpha methyl styrene or a methy or other $C_2-C_4$ lower alkyl homologue thereof or hydrogenated derivative thereof or mixture of same, having one of the generic structures:

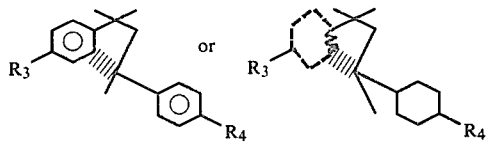

wherein $R_3$ and $R_4$ are the same or different and each represents hydrogen or methyl or other $C_2-C_4$ lower alkyl and wherein the dashed lines and wavy lines represent carbon-carbon single bonds or carbon-carbon double bonds with the proviso that when there is one double bond present only the wavy line is a double bond and when there is more than one double bond present, the ring containing the dashed lines and the wavy line is a benzene ring and wherein the line |||||||||| represents either a carbon-carbon single bond or no bond.

Nothing in the prior art teaches the use of acetylated alpha methyl styrene dimers, methyl homologues thereof or hydrogenated derivatives thereof as perfume diluents or as perfume extenders. Furthermore, nothing in the prior art teaches the use of hydrogenated derivatives of such acetylated alpha methyl styrene dimers or methyl homologues thereof.

BRIEF DESCRIPTION OF THE DRAWINGS

FIG. 9 is the GLC profile for the product produced according to Example IV, bulked fractions 5-11.

FIG. 10 is the GLC profile for the product produced according to Example V, bulked fractions 8-14.

THE INVENTION

Figure 1:
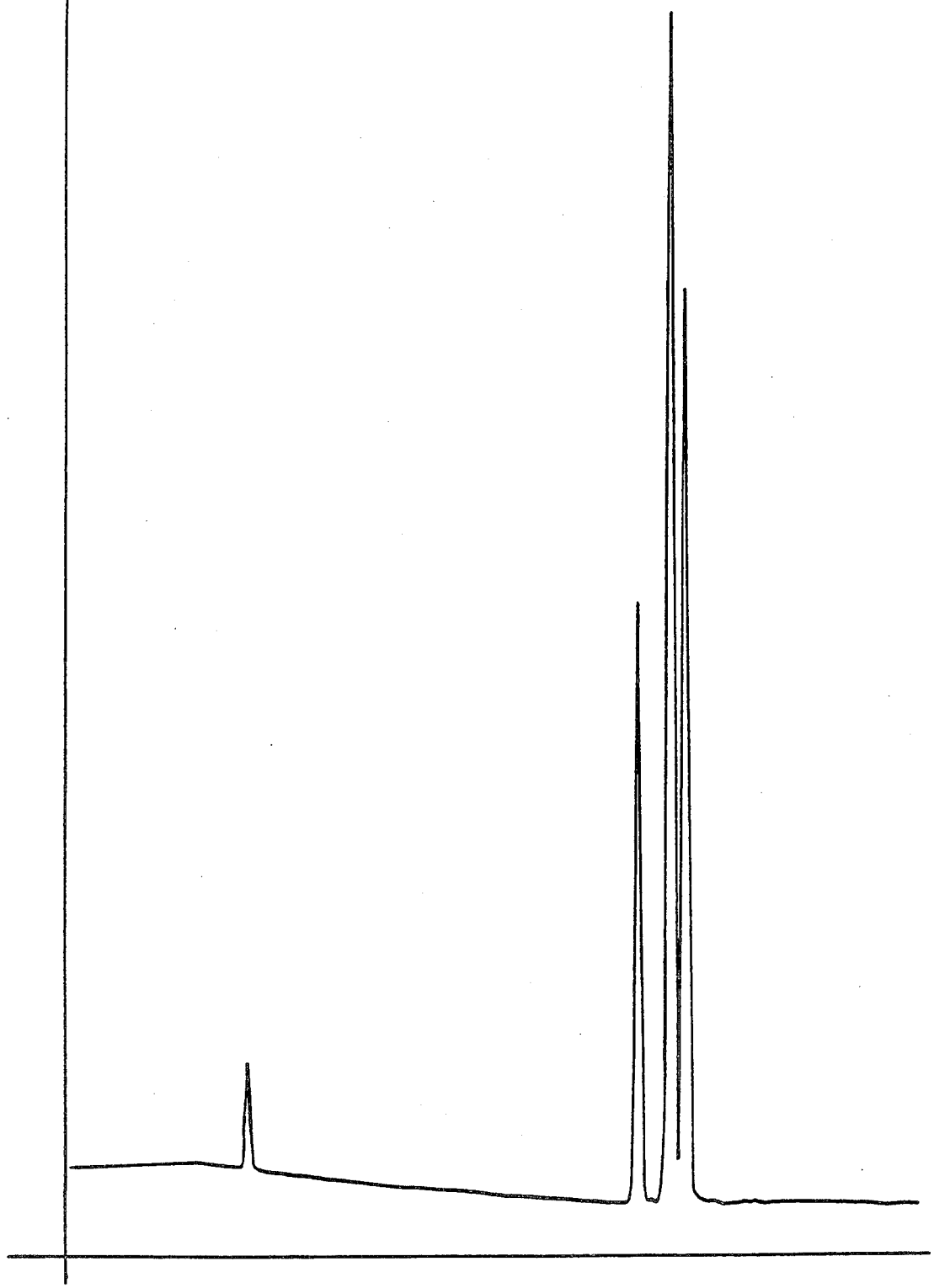
FIG. 1 is the GLC profile for the product produced according to FIG. I, Fraction 19.

Surprisingly, it has been found that acetylated alpha methyl styrene dimerization products, acetylated dimerization products of methyl or other $C_2-C_4$ lower alkyl homologues thereof and hydrogenated derivatives thereof may be used as diluents or extenders of various perfumery materials without appreciable loss of the characteristic odor effect of such perfumery materials. Such dimerization products are produced by first dimerizing alpha methyl styrene having the structure:

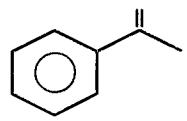

or by dimerizing a methyl or other $C_2-C_4$ lower alkyl homologue thereof having, for example, the structure:

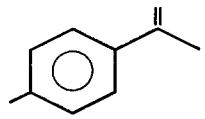

in the presence of Lewis Acid catalysts, Bronstedt acid catalysts such as sulfuric acid or in the presence of acid clay catalysts such as Japanese Acid Clay or Fullers earth or acidic cation exchange resin catalysts. The dimerization product of alpha methyl styrene so produced have the structures:

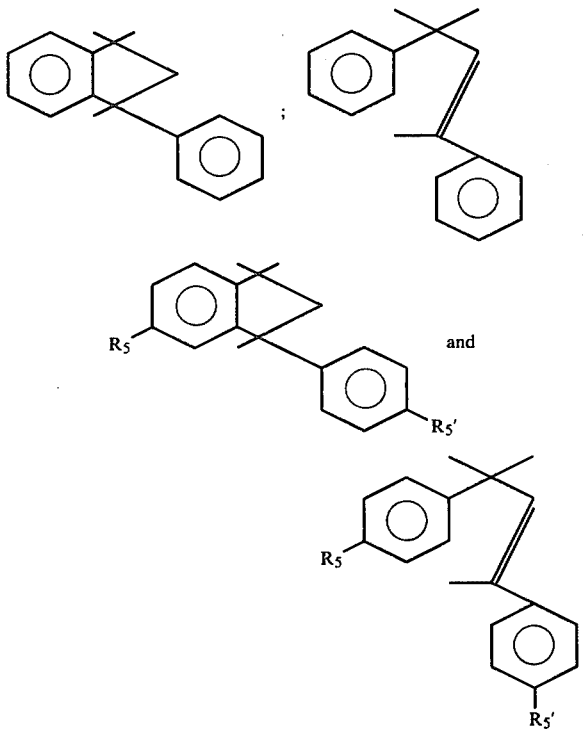

wherein one of $R_5$ or $R'_5$ is methyl or other $C_2-C_4$ lower alkyl and the other of $R_5$ or $R'_5$ is hydrogen or each of $R_5$ and $R'_5$ are the same or different $C_1-C_4$ lower alkyl, e.g., methyl.

The resulting dimerization products are then acetylated using acetyl chloride or acetyl bromide in the presence of a Lewis acid catalyst, such as aluminum chloride.

Hydrogenation products thereof have the structures:

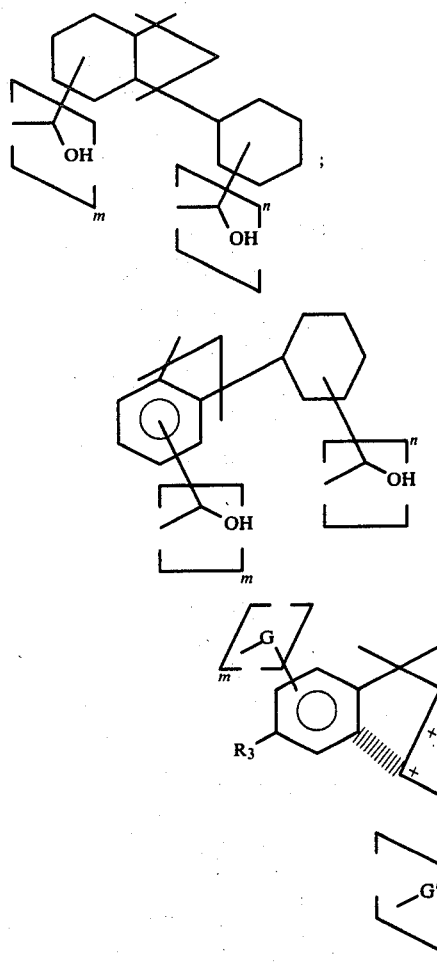
(wherein $R_3$ and $R_4$ are the same or different and each represents hydrogen, methyl or other $C_2$–$C_4$ lower alkyl and wherein G is one of the moieties:
with at least one of G being a moiety having the structure:
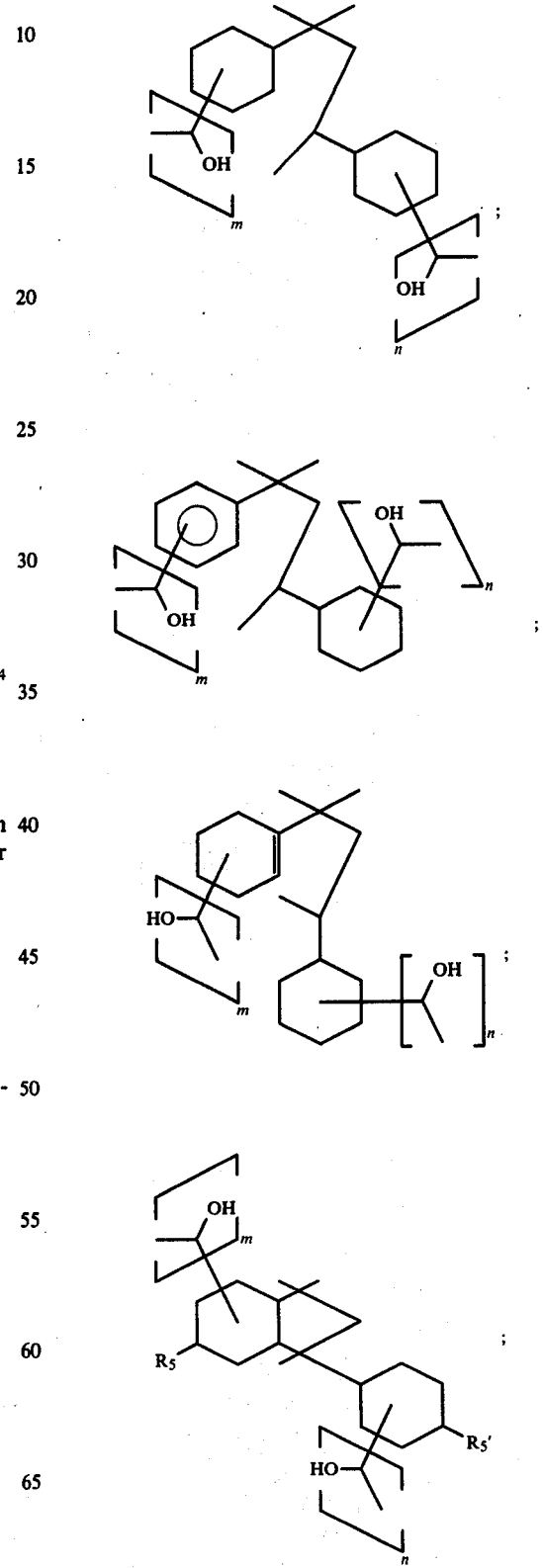

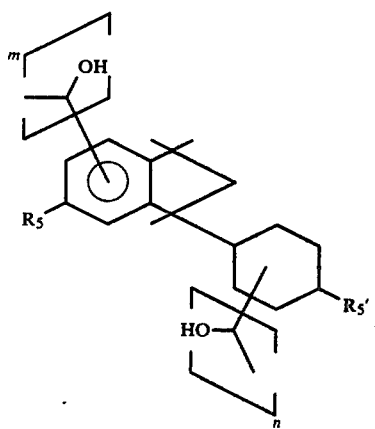
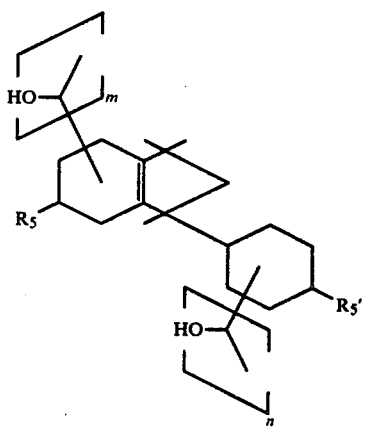
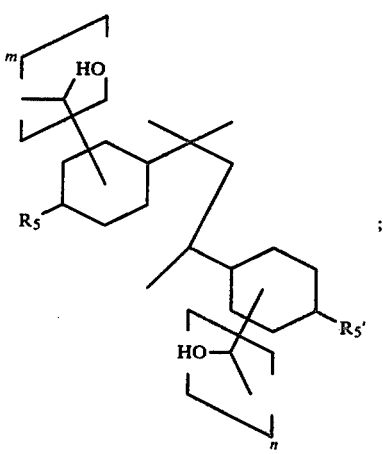
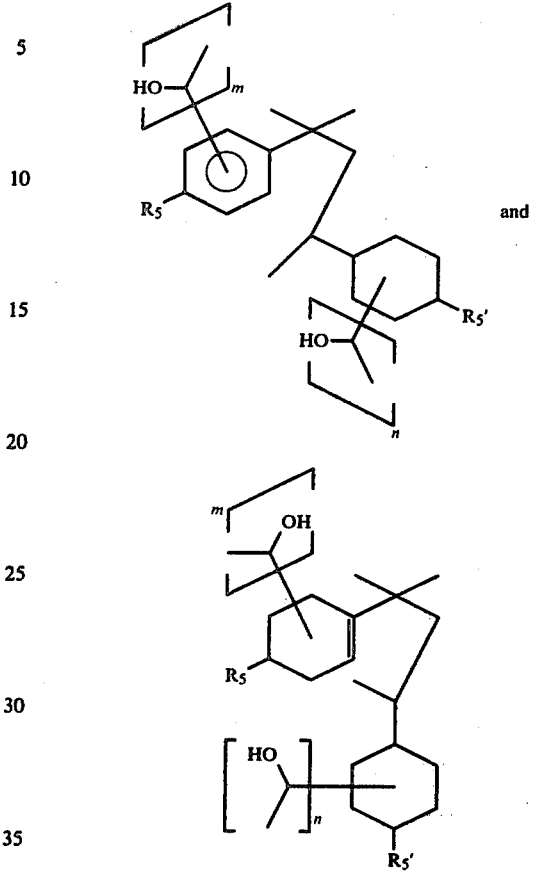
wherein one or both of $R_5$ and $R'_5$ is methyl or other $C_2$–$C_4$ lower alkyl and wherein n=0 or 1 and m=0 or 1 and the sum of m+n is such that the inequality:
$$0 < m+n \leq 2$$
is in effect. Such hydrogenation products can be represented by the generic structure:
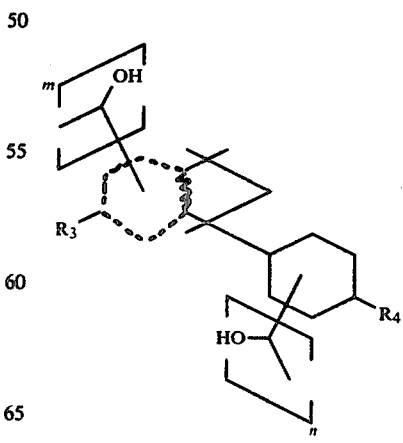

-continued wherein $R_3$ and $R_4$ are the same or different and represent hydrogen or methyl or other $C_2$–$C_4$ lower alkyl; wherein the dashed lines and wavy line represent carbon-carbon single bonds or carbon-carbond double bonds with the proviso that when there is one double bond present, only the wavy line is a double bond and when there is more than one double bond present, the ring containing the dashed lines and the wavy line is a benzene ring and where the line ||||||| represents either a carbon-carbon single bond or no bond.

Contemplated in this case are geometric isomers of the hydrogenation products of our invention. Thus, in the case of the hydrogenation product, when $R_3$ and/or $R_4$ are lower alkyl, for example, methyl, the methyl groups may be in a "cis" or "trans" relationship to one another and with respect to the hydroxy alkyl group or groups.

A significant property of the above-said dimerization products and hydrogenated dimerization products is that they have a broad range of solubilities for various types of perfumery materials including complete solubility for certain alcohols, esters, pyrans, aldehydes, ketones, cyclic ethers, cyclic amines, nitriles and natural oils. Thus, for example, the following materials are completely miscible with the dimers which are the subject of our invention.

Phenyl Ethyl Alcohol
Geraniol
Terpineol
Citronellyl Acetate
Decyl Acetate
Rose Oxide
n-Decanal
Citral
Alpha Ionone
Eugenol
Galaxolide
2-Methyl-2-Pentenoic Acid
Isobutyl Quinoline
Lemon Oil
Rosemary Oil
Patchouli Oil
Cinnamonitrile
Geranonitrile Thus, it has been discovered that the dimers of our invention can be used as partial replacements for certain essential oils and synthetic substitutes therefor in compounded single phase liquid perfumery compositions.

Accordingly, the present invention comprises a compounded single phase liquid perfumery composition which comprises one or more synthetic perfume oils or natural perfume oils or mixtures of natural perfume oils and synthetic perfume oils with which there has been incorporated from about 1 up to about 30 parts of an acetylated alpha methyl styrene or alpha methyl styrene methyl or other $C_2$–$C_4$ lower alkyl homologue dimerization product or hydrogenated derivative thereof or mixture of acetylated alpha methyl styrene or alpha methyl styrene methyl (or other $C_2$–$C_4$ lower alkyl) homologue dimerization product and one or more hydrogenated derivatives thereof which have at least one of the following structues:

-continued
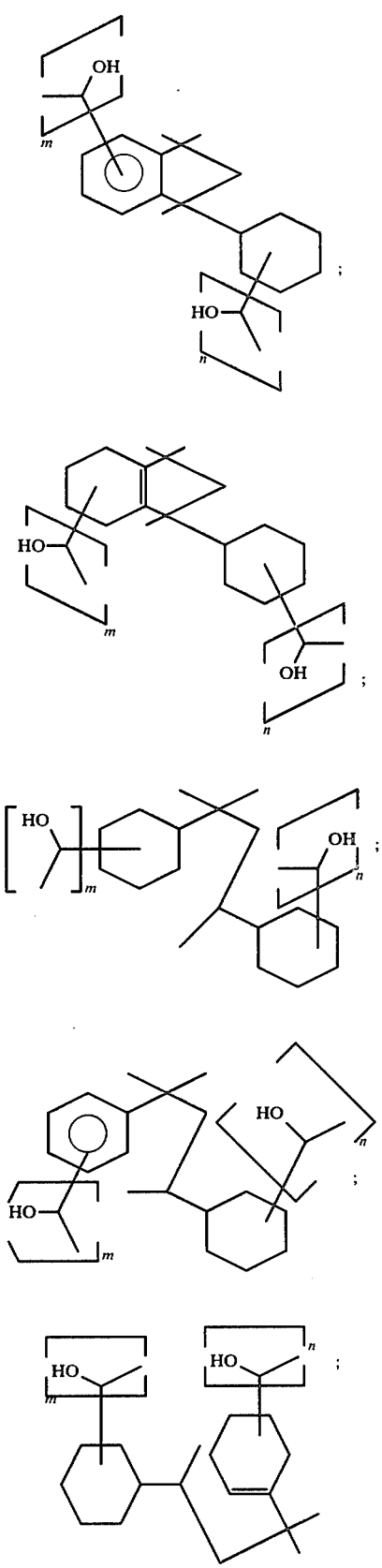
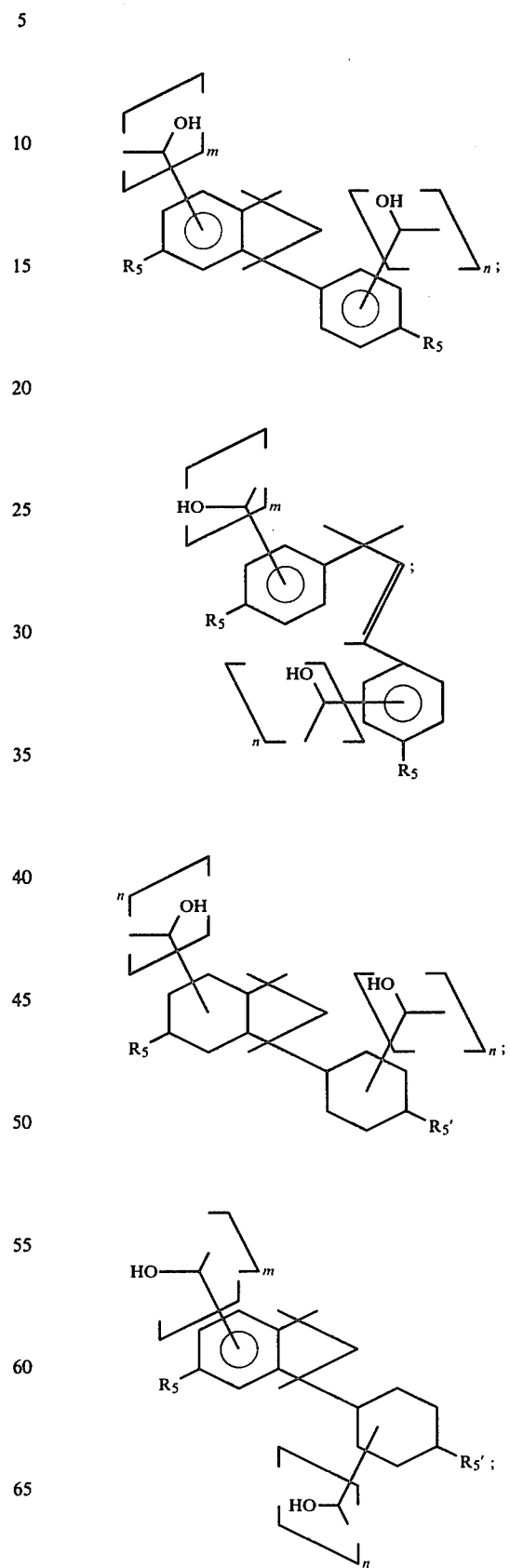

-continued
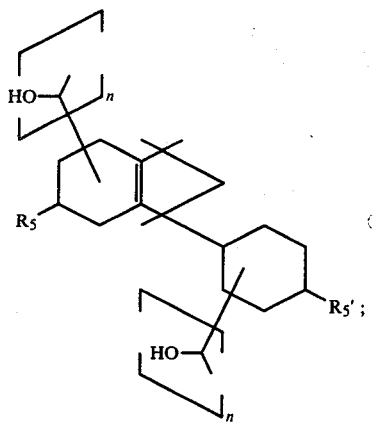
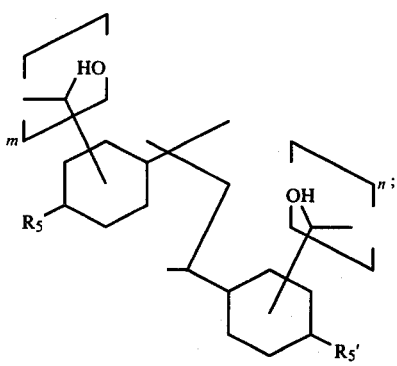
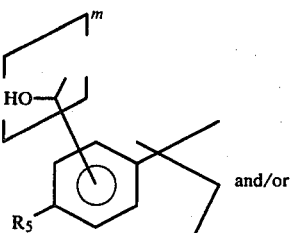
and/or
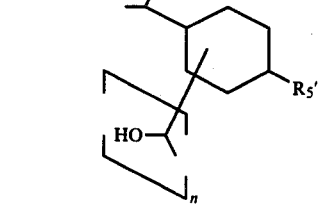
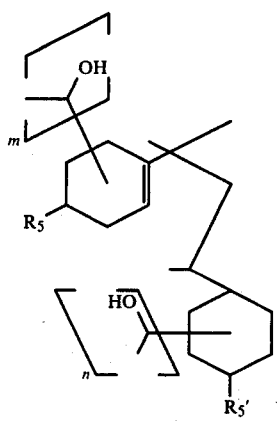
wherein one or both of $R_5$ and $R'_5$ is methyl or other $C_2$–$C_4$ lower alkyl and these compounds may be represented collectively by the generic structures:
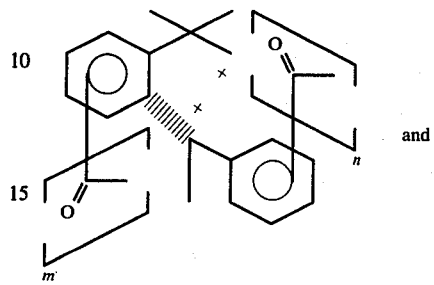
and
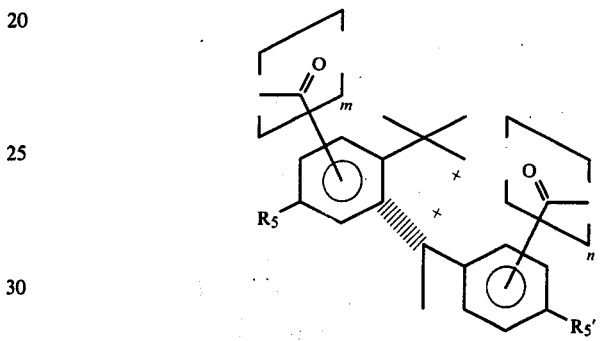
in the case of acetylated alpha methyl styrene dimerization products and dimerization products of methyl or other $C_2$–$C_4$ lower alkyl homologues thereof and the structures:
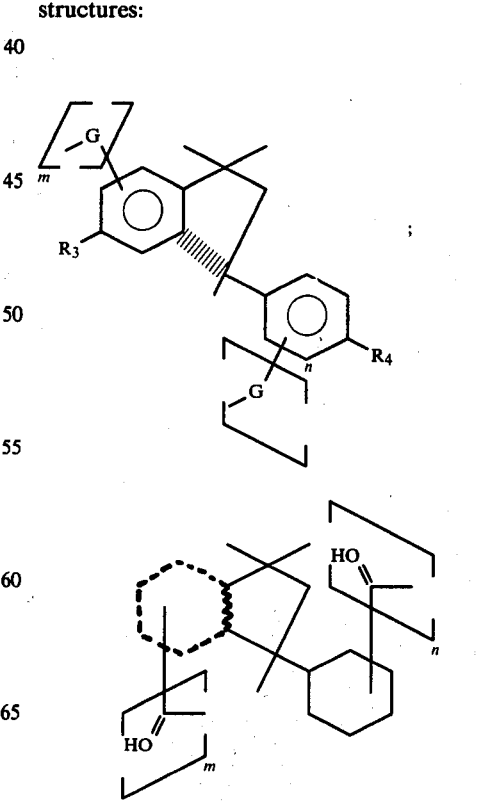

-continued

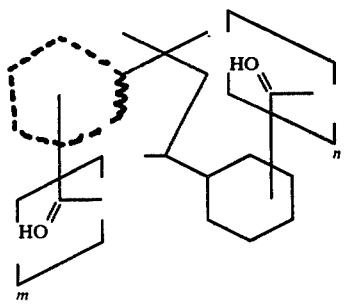

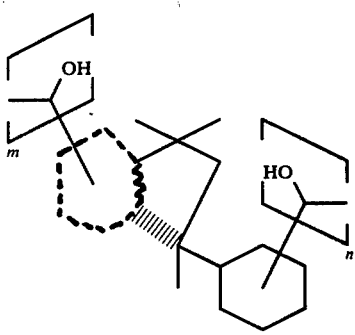

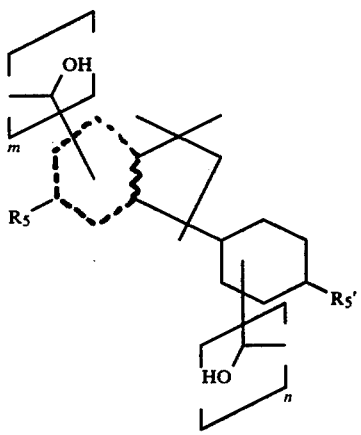

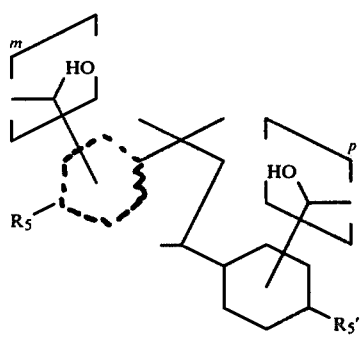

-continued

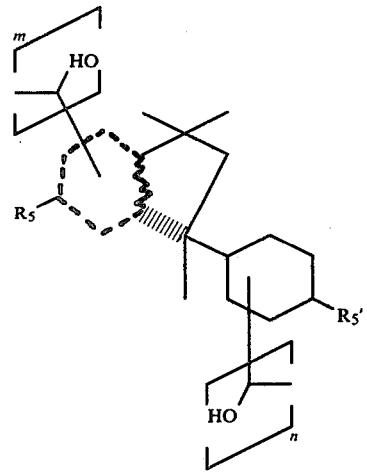

wherein m=0 or 1 and n=0 or 1 and m+n are further defined by the mathematical inequality:

$0 < m+n \leq 2$;

wherein one of $R_5$ and $R'_5$ is methyl or other $C_2$–$C_4$ lower alkyl and the other is hydrogen, or both $R_5$ and $R'_5$ are methyl or other $C_2$–$C_4$ lower alkyl in the case of the hydrogenated derivatives thereof wherein the dashed lines and wavy lines represent carbon-carbon single bonds or carbon-carbon double bonds with the proviso that when there is one double bond present in the ring containing the dashed lines and wavy lines, only the wavy line is a double bond and when there is more than one double bond present, the ring containing the dashed lines and the wavy lines is a benzene ring; and wherein the line ||||||||||| represents either a carbon-carbon single bond or no bond; and wherein the line + + + + represents a carbon-carbon single bond or a carbon-carbon double bond with the proviso that when the line + + + + is a carbon-carbon double bond, the line ||||||||| is no bond and when the line + + + + is a carbon-carbon single bond, the line ||||||||| is a carbon-carbon single bond, per 100 parts of compounded single phase liquid perfumery composition.

Each of these acylated dimerization products and hydrogenated derivatives thereof by themselves have no odor which is perceptible to the human olfactory sense of smell at ambient conditions and do not by themselves impart any alteration of odor to any of the perfumery materials to which they are added alone or in combination with one another. The above-stated acylated dimerization products and hydrogenated derivatives thereof may be produced according to any of the known methods in the prior art and according to any one of the following reaction schemes:

Reaction Scheme #1:
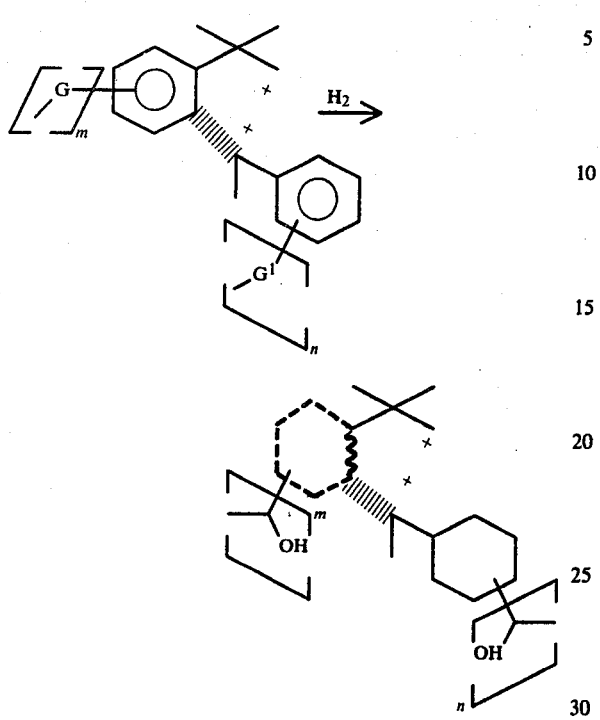
Reaction Scheme #2:
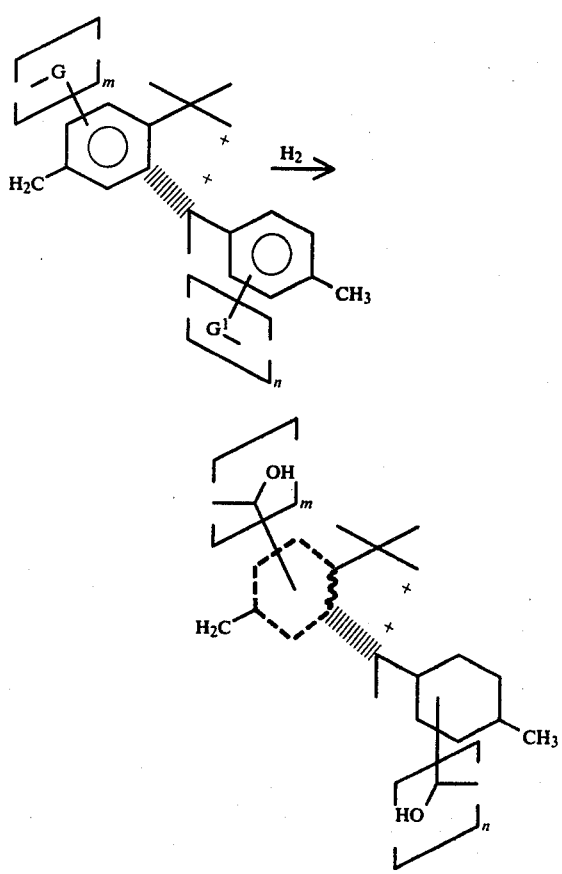
Reaction Scheme #3:
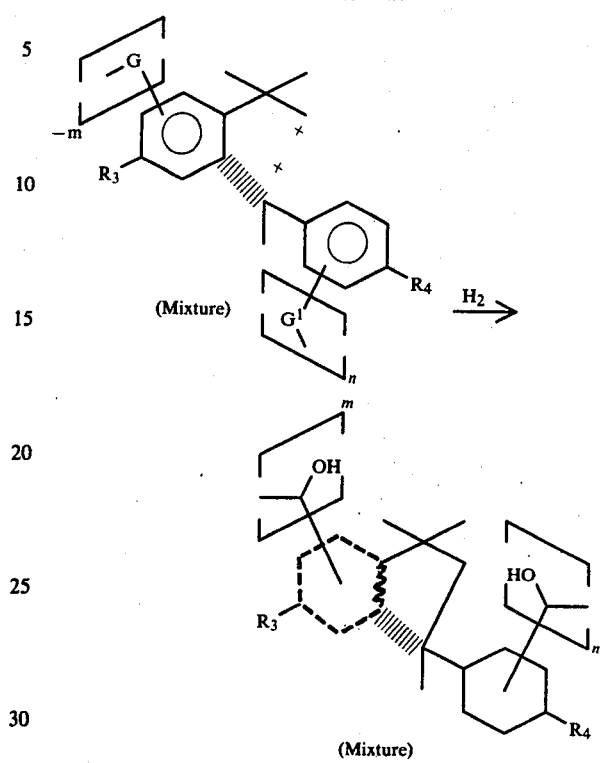
Reaction Scheme #4:
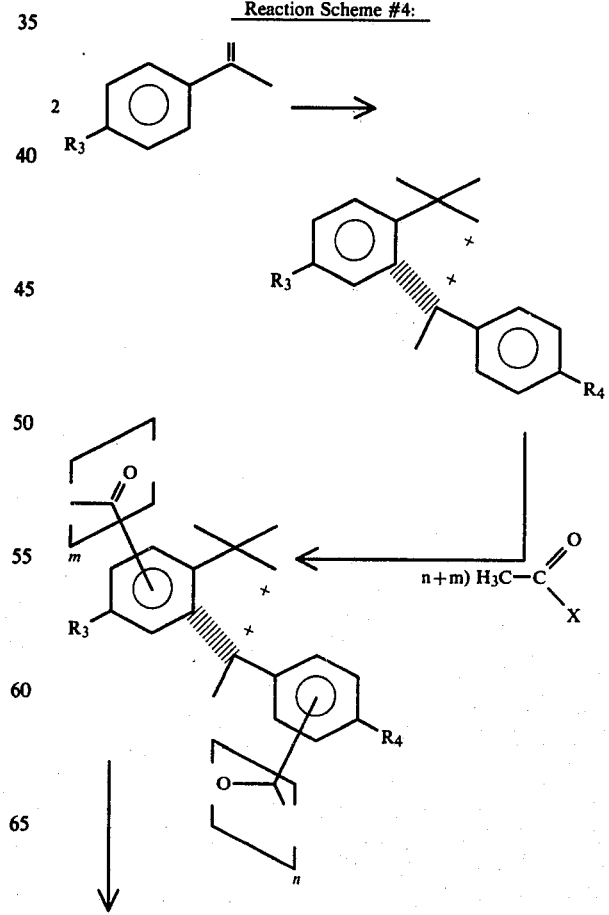

-continued
Reaction Scheme #4:

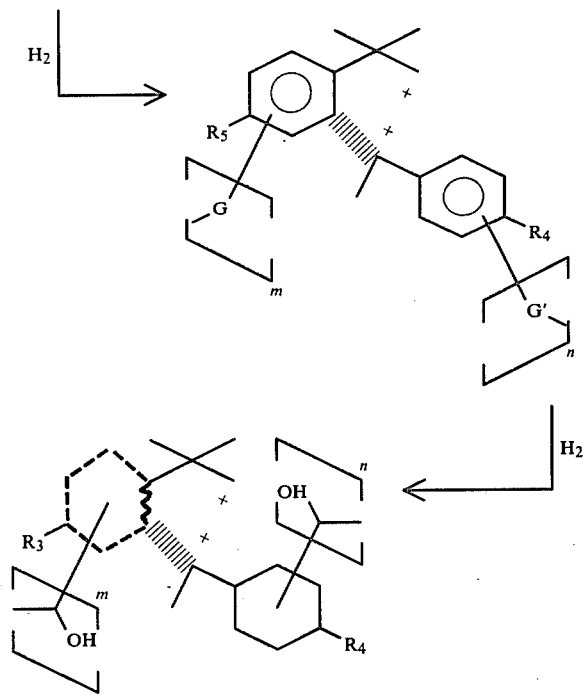

wherein n=0 or 1 and m=0 or 1 and the sum of m+n is such that the inequality:

0<m+n≦2 is in effect; wherein G is one of the moieties:

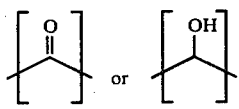

with at least one of G being a moiety having the structure:

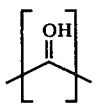

and wherein $R_3$ and $R_4$ are the same or different and repesent hydrogen or methyl or other $C_2$-$C_4$ lower alkyl and wherein the dashed lines, the wavy lines, and the line ‖‖‖‖‖ and the line++++are as defined above.

In the dimerization reaction, the catalysts that may be used are Lewis Acid such as borontrifluoride-aluminum trichloride or Bronstedt Acids such as sulfuric acid or phosphoric acid or such acids on carriers such as alumina, silica or cation exchange resin catalysts such as Amberlyst ® 15, or acid clay catalysts such as Japanese Acid clay or Fullers earth. The dimerization reaction is carried out in the presence of a solvent such as cyclohexane, or in the absence of solvent. The temperature range for the dimerization may be from about 20° C. up to about 250° C. with a preferred temperature range when using borontrifluoride etherate of 0°-100° C. or when using acid clays of from 80°-200° C. The presence at which the reaction may be carried out is conveniently atmospheric pressure but higher pressures or pressures lower than atmospheric may also be used without adversely affecting the yield of product. The weight ratio of alpha methyl styrene or alphe methyl styrene methyl homologue:catalyst is from about 1:0.005 up to about 1:0.2 when using an acid clay catalyst and from about 1:0.1 up to about 1:3 when using, for example, a Bronstedt acid catalyst such as sulfuric acid.

The hydrogenation reaction may be carried out at standard hydrogenation conditions using standard hydrogenation catalysts. Thus, for example, the hydrogenation reaction is carried out in the presence of a palladium on carbon catalyst or a Raney nickel catalyst at temperatures of from about 80° C. up to about 150° C. at pressures of from about four atmospheres up to about thirty atmospheres. Such catalysts such as palladium (from 1% up to 10%) on calcium carbonate in the presence of an inert solvent, such as ethyl acetate, and catalyst promoter, such as quinoline, or palladium (from 1% up to 10%) on barium sulfate are particularly preferred. The mole ratio of catalyst:catalyst promoter, e.g., palladium on barium sulfate-quinoline is preferaby about 1:1 (weight:weight) but ratios of catalyst:promoter may vary from about 0.25:1 up to about 1:0.25. The weight ratio of material to be hydrogenated:inert solvent (e.g., ethyl acetate) may vary from about 1:1 up to about 1:20 with a ratio of about 1:10 (weight:weight) being preferred. At the end of the reaction, the reaction product may, if desired, be separated by means of such physical separation techniques as fractional distillation.

The extended perfumery oils and chemicals of our invention may be used in compositions where the natural oils or chemicals would have been used, for example, in combination with sandalwood oil, vetiver oil, oakmoss, ionone, labdanum, methyl ionone, patchouli oil and other synthetic substitutes therefor.

The extended perfumery materials of our invention will find use as constituents of compounded perfumery compositions in which a number of perfumery materials of natural and/or synthetic origin will be blended together to produce a particular desired odor effect. Such compositions may then be used in space sprays or can be blended in soap, detergent or deodorant compositions, including bath salts, shampoos, toilet waters, face creams, talcum powders, body lotions, sun cream preparations and shave lotions and creams. The perfumery compositions can also be used to perfume sub-straights such as fibers, fabrics and paper products.

The following examples are given to illustrate embodiments of the invention as it is presently preferred to practice it. It will be understood that these examples are illustrative and the invention is not to be considered as restricted thereto except as indicated in the appended claims.

EXAMPLE I

PREPARATION OF ALPHA METHYL STYRENE DIMERIZATION PRODUCT

Reaction:

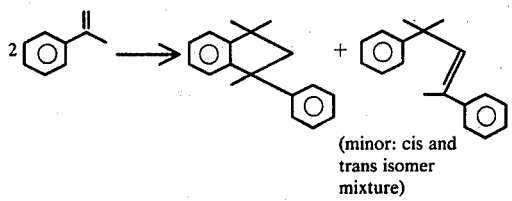

(minor: cis and trans isomer mixture)

Into a two-liter reaction flask equipped with thermometer, reflux condenser, cooling bath, addition funnel, stirrer and gas bubbler is placed 100 g of water. Over a sixteen-minute period, 318 g of concentrated sulfuric acid is added to the water. The contents of the flask is then brought to 30° C. Over a period of two hours after the sulfuric acid is added, while maintaining the temperature of the reaction mass at 20°-33° C., 500 g of alpha methyl styrene is added. After the addition of the alpha methyl styrene, the reaction mass is maintained at a temperature of 30° C. for a period of four hours. 500 g of water is then added followed by 250 g of cyclohexane. The reaction mass is then stirred for a period of fifteen minutes and heated to 70° C. The layers are separated and the organic layer is washed neutral (at 70° C.) with a 5% sodium hydroxide solution (two 250 ml volumes) and a 5% sodium chloride solution (three 250 ml volumes). 650 g of crude product is recovered and redistilled after adding to the mixture 15 g of Primol ® and 0.2 g of Ionox ® through a 12" Vigreaux column as follows:

| Fraction | Vapor Temp. | Liquid Temp. | Vac. mm. | Weight of Fraction |
|---|---|---|---|---|
| 1 | 69 | 101/135 | 760/760 | 102.2 |
| 2 | 132 | 145 | 2.3 | 2.8 |
| 3 | 132 | 146 | 2.3 | 26.4 |
| 4 | 132 | 147 | 2.3 | 16.0 |
| 5 | 132/134 | 148/148 | 2.2/2.2 | 19.4 |
| 6 | 132 | 149 | 2.2 | 26.2 |
| 7 | 132 | 149 | 2.2 | 21.6 |
| 8 | 132 | 142 | 2.2 | 25.4 |
| 9 | 132 | 150 | 2.2 | 24.2 |
| 10 | 133 | 150 | 2.2 | 29.6 |
| 11 | 133 | 151 | 2.5 | 28.2 |
| 12 | 133 | 151 | 2.4 | 25.5 |
| 13 | 133 | 152 | | 25.0 |
| 14 | 133 | 152 | 2.3 | 23.7 |
| 15 | 133 | 155 | | 31.5 |
| 16 | 135 | 162 | 2.3 | 29.4 |
| 17 | 137 | 169 | 2.3 | 23.1 |
| 18 | 139 | 176 | 2.3 | 12.5 |
| 19 | 142 | 202 | | 13.2 |
| 20 | 141 | 221 | 2.3 | 10.3 |
| 21 | 188 | 230 | | 10.5 |
| 22 | 187 | 242 | 2.3 | 8.1 |

FIG. 1 sets forth a GLC profile for Fraction 19. This fraction is primarily the alpha methyl styrene dimer having the structure:

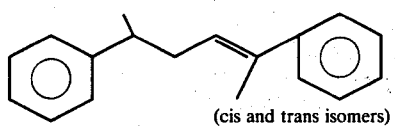

(cis and trans isomers)

Figure 2:
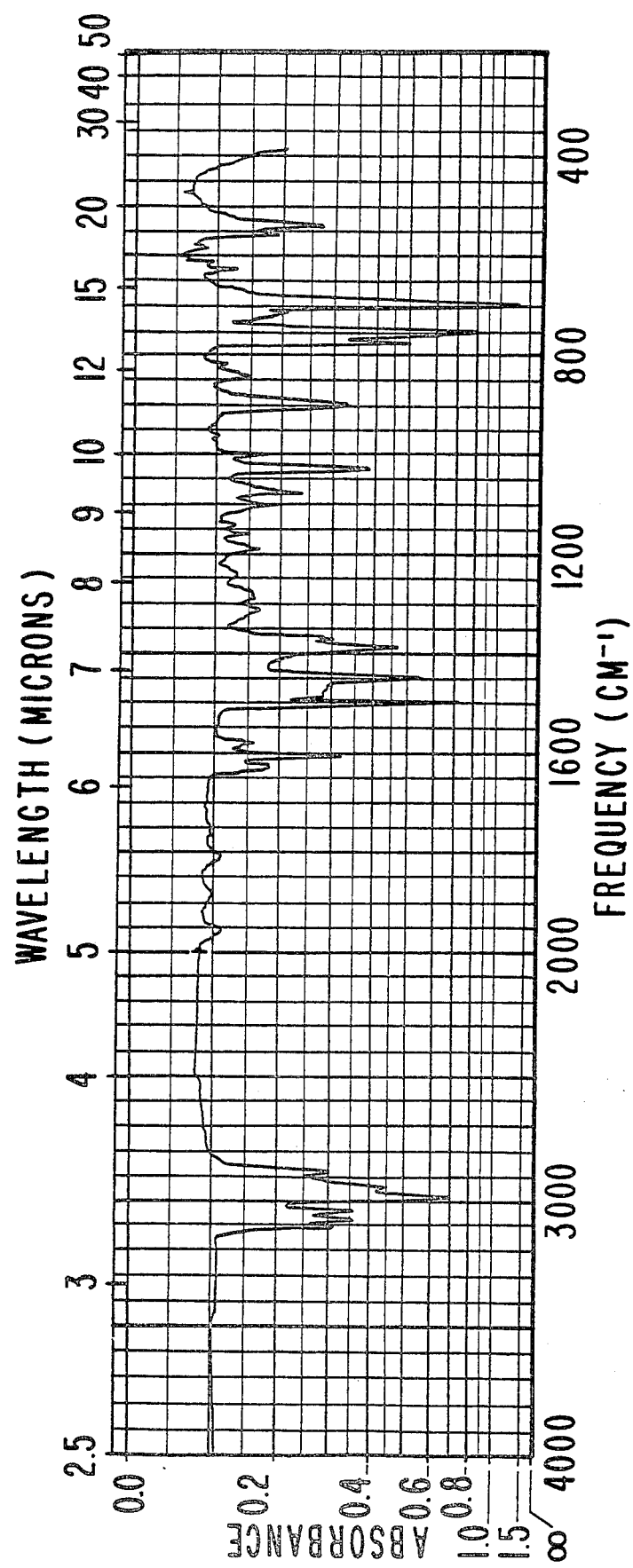
FIG. 2 is the infrared spectrum for the product produced according to Example I, Fraction 19.
Figure 3:
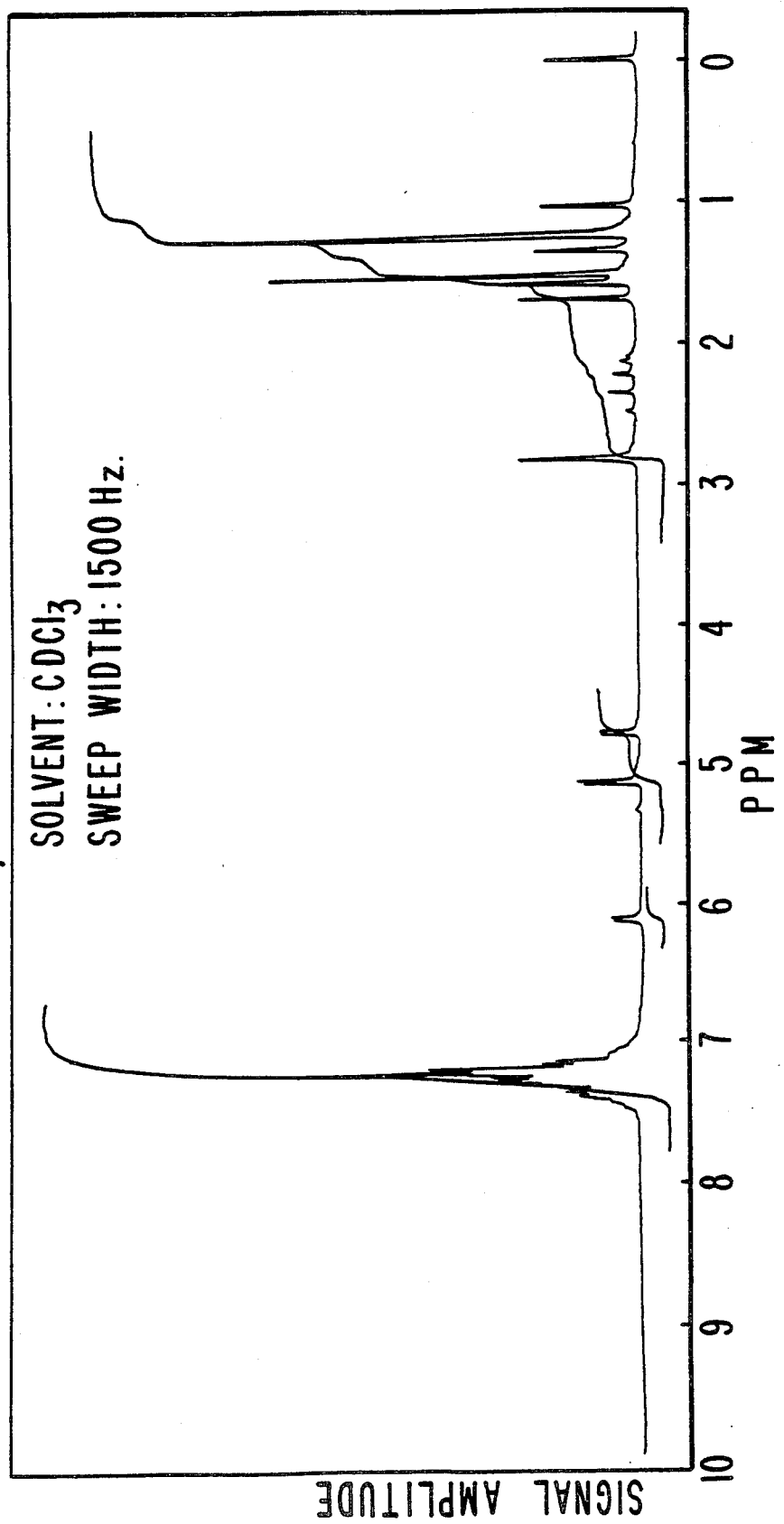
FIG. 3 is the NMR spectrum for the product produced according to Example I, Fraction 19.

FIG. 2 is the infrared spectrum for Fraction 19. FIG. 3 is the NMR spectrum for Fraction 19. The mass spectrum for Fraction 19 which is the compound having the structure:

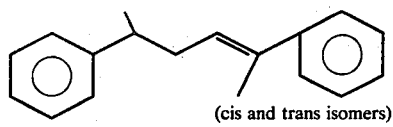

(cis and trans isomers)

is as follows:

| M/E | Relative Intensity |
|---|---|
| 39 | 23[5] |
| 41 | 27[4] |
| 51 | 18 |
| 77 | 19 |
| 91 | 42[2] |
| 103 | 14 |
| 119 | 100[1] |
| 143 | 20 |
| 221 | 32[3] |
| 236 | 20[6] |

Figure 4:
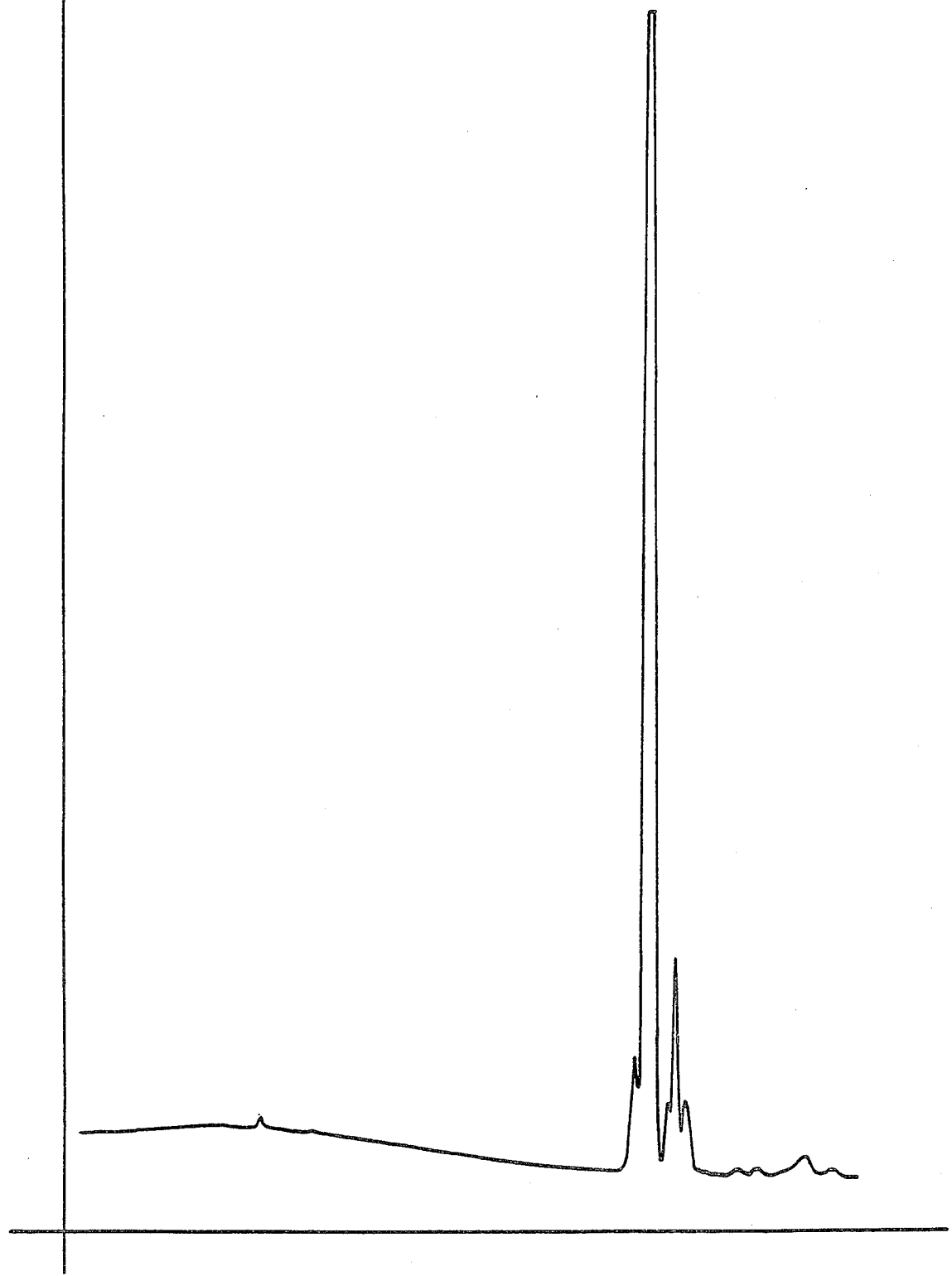
FIG. 4 is the GLC profile for the product produced according to Example I, Fraction 3.
Figure 5:
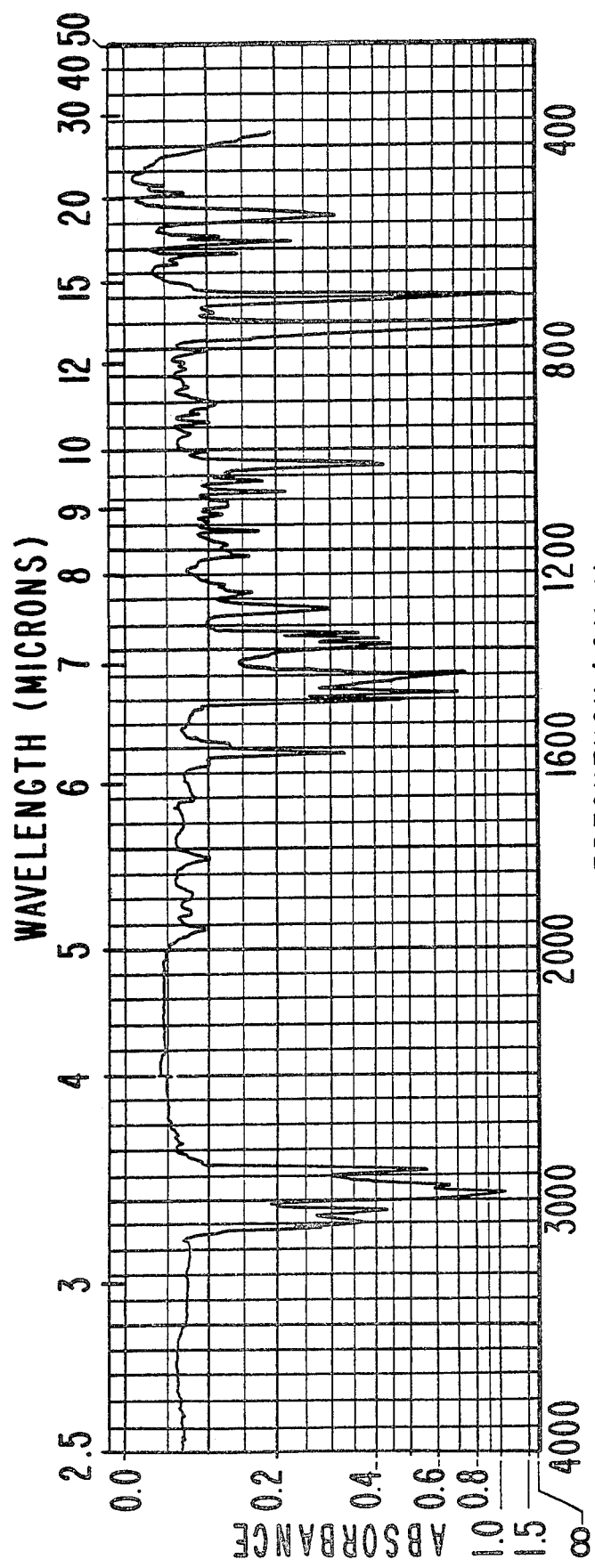
FIG. 5 is a the infrared spectrum for the product produced according to Example I, Fraction 3 as well as Example III.
Figure 6:
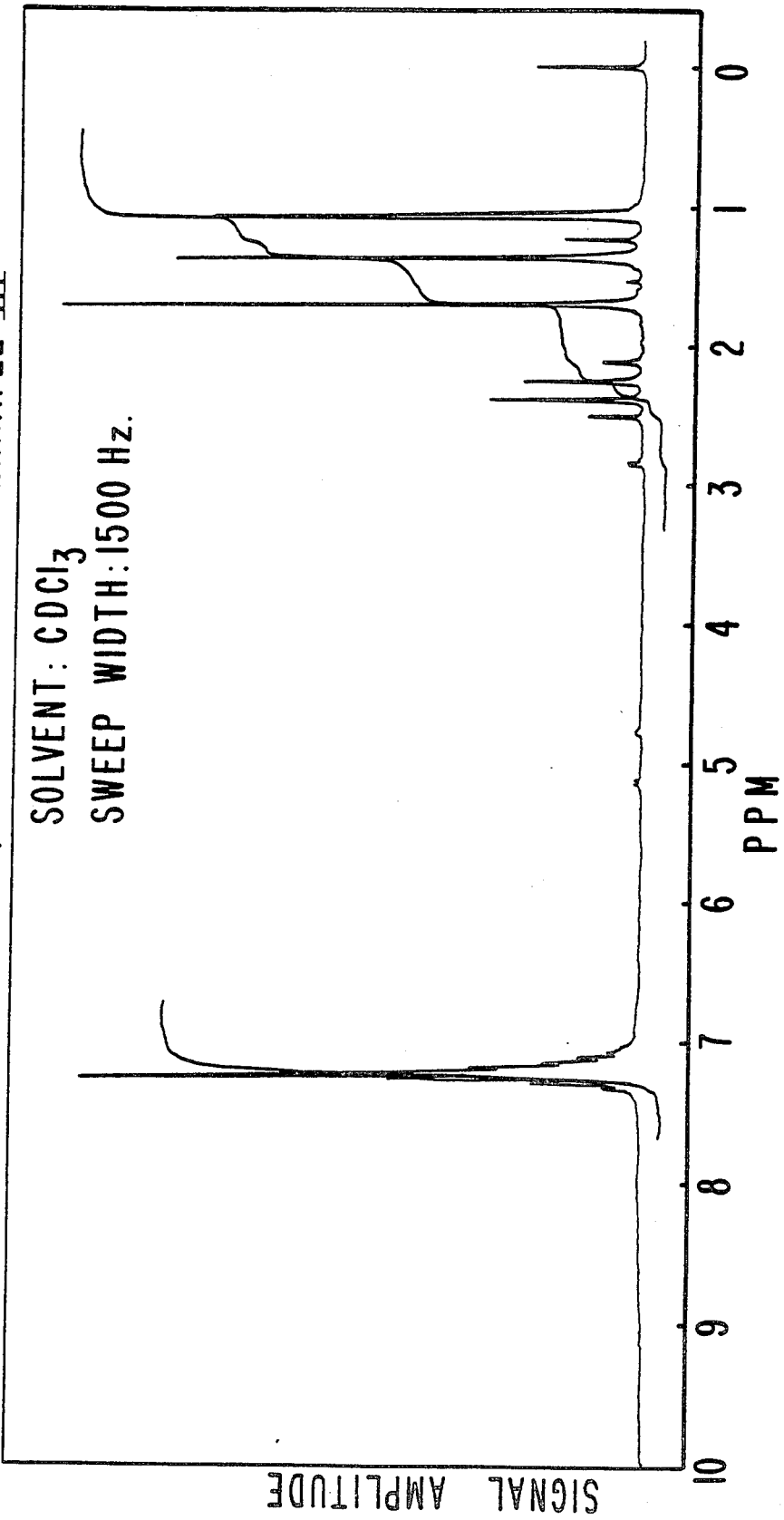
FIG. 6 is the NMR spectrum for the product produced according to Example I, Fraction 3, as well as the product produced according to Example III.

The GLC profile for Fraction 3 which is primarily the compound having the structure:

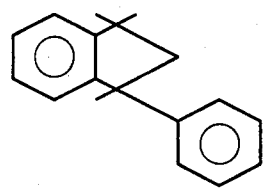

is set forth in FIG. 4. FIG. 5 sets forth the infrared spectrum for Fraction 3. FIG. 6 sets forth the NMR spectrum for Fraction 3.

FIGS. 4, 5 and 6 also represent, respectively, the GLC, IR and NMR spectra for the product produced according to Example III, infra.

EXAMPLE II

PREPARATION OF ALPHA METHYL STYRENE DIMERIZATION PRODUCT

Reaction:

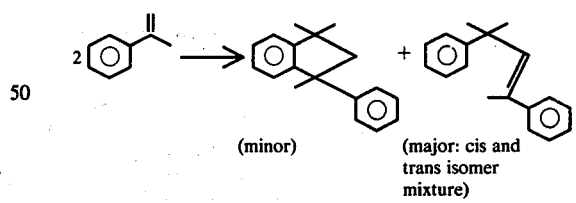

(minor)    (major: cis and trans isomer mixture)

Into a one-liter reaction flask equipped with thermometer, addition funnel, heating mantle, reflux condenser, stirrer, Y-adapter and distillation head is added 100 g of cyclohexane followed by 5 g of p-toluene sulfonic acid. The resulting mixture is heated to 50° C. and over a one-hour period, 500 g of alpha metal styrene is added to the reaction flask. The reaction mass is then heated to 100° C. and maintained at that temperature for a period of four hours. 529.3 g of crude product is then recovered which is then mixed with 15 g of Primol ® and 0.2 g of Ionox ®. The resulting mixture is distilled through a "Y" adapter distillation column yielding the following distillation data:

| Fraction | Vapor Temp. | Liquid Temp. | Vac. mm. | Weight of Fraction |
|---|---|---|---|---|
| 1 | 21/80 | 90/149 | 2.6/2.5 | 6.4 |
| 2 | 139 | 155 | 2.5 | 7.0 |
| 3 | 139 | 155 | 2.5 | 21.4 |
| 4 | 140 | 157 | 2.5 | 34.0 |
| 5 | 142 | 160 | 2.4 | 49.6 |
| 6 | 144 | 170 | 2.4 | 100.4 |
| 7 | 164 | 195 | 2.4 | 58.5 |
| 8 | 174 | 203 | 2.2 | 8.0 |
| 9 | 200 | 215 | 3.5 | 70.0 |
| 10 | 202 | 215 | 2.2 | 31.3 |
| 11 | 206 | 215 | 2.2 | 27.1 |
| 12 | 214 | 225 | 2.2 | 18.1 |
| 13 | 210 | 250 | 2.2 | 41.6 |

EXAMPLE III

PREPARATION OF ALPHA METHYL STYRENE DIMER

Reaction:

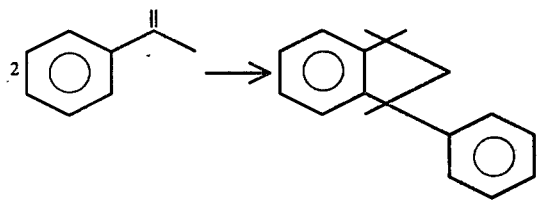

Into a 1,000 ml reaction flask equipped with thermometer, addition funnel, heating mantle, reflux condenser and stirrer is added 20 g of Filgrol 25 (a 10–20 mesh granular acid activated clay produced by the Filtrol Corporation of 5959 West Century Boulevard, Los Angeles, California 90045) having the following properties:

| Particle size analysis by Tyler Standard Sieve | |
|---|---|
| Through 10 Mesh, Wt. % | 100 |
| Through 20 Mesh, Wt. % | 5 |
| Free Moisture, Wt. % | 10 |
| Free and Combined Moisture, Wt. (Los at 1700° F.) | 15 (Max.) |
| Bulk Density, lbs./cu. ft. | 43.0 |
| Particle Density | 1.3 |
| Surface Area, N₂ adsorbent (Bet Method) M²/gm | 280–300 |

50 g of alpha methyl styrene is added to the Filtrol and the reaction mass is heated to 100° C. Another 450 g of alpha methyl styrene is then slowly added to the reaction mass over a period of two hours. The reaction mass is then heated to 150° C. and maintained at that temperature for a period of four hours. The reaction mass is then filtered yielding 470 g of crude product which is then mixed with 12 g Primol ® and 0.3 g Ionox ® and distilled through a 10" Vigreaux column, yielding the following fractions and the following distillation data:

| Fraction | Vapor Temp. | Liquid Temp. | Vac. mm. | Weight of Fraction (gm) |
|---|---|---|---|---|
| 1 | 38/88 | 135/140 | 2.5/2.5 | 1.2 |
| 2 | 133 | 142 | 2.0 | 7.0 |
| 3 | 134 | 142 | 2.0 | 12.0 |
| 4 | 134 | 142 | 2.0 | 17.1 |
| 5 | 134 | 145 | 1.8 | 53.5 |
| 6 | 134 | 146 | 1.8 | 31.0 |
| 7 | 135 | 147 | 1.8 | 49.2 |
| 8 | 135 | 148 | 1.8 | 51.5 |
| 9 | 136 | 149 | 1.8 | 46.2 |
| 10 | 137 | 151 | 1.8 | 52.3 |
| 11 | 137 | 159 | 1.8 | 43.2 |
| 12 | 139 | 170 | 1.8 | 17.5 |
| 13 | 185 | 225 | 1.8 | 21.6 |
| | | | | (Residue 40.3 g) |

Figure 7:
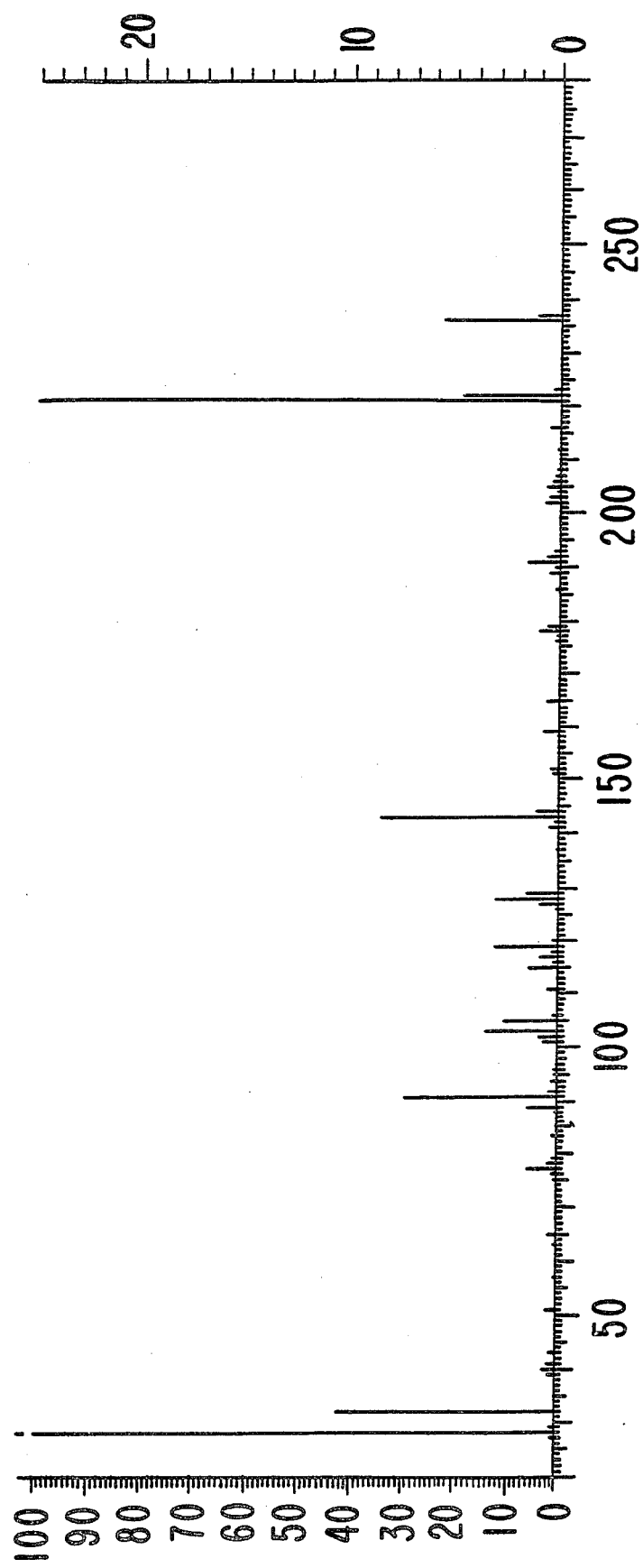
FIG. 7 is the mass spectrum for the product produced according to Example I, Fraction 3, as well as the product produced according to Example III.
Figure 8:
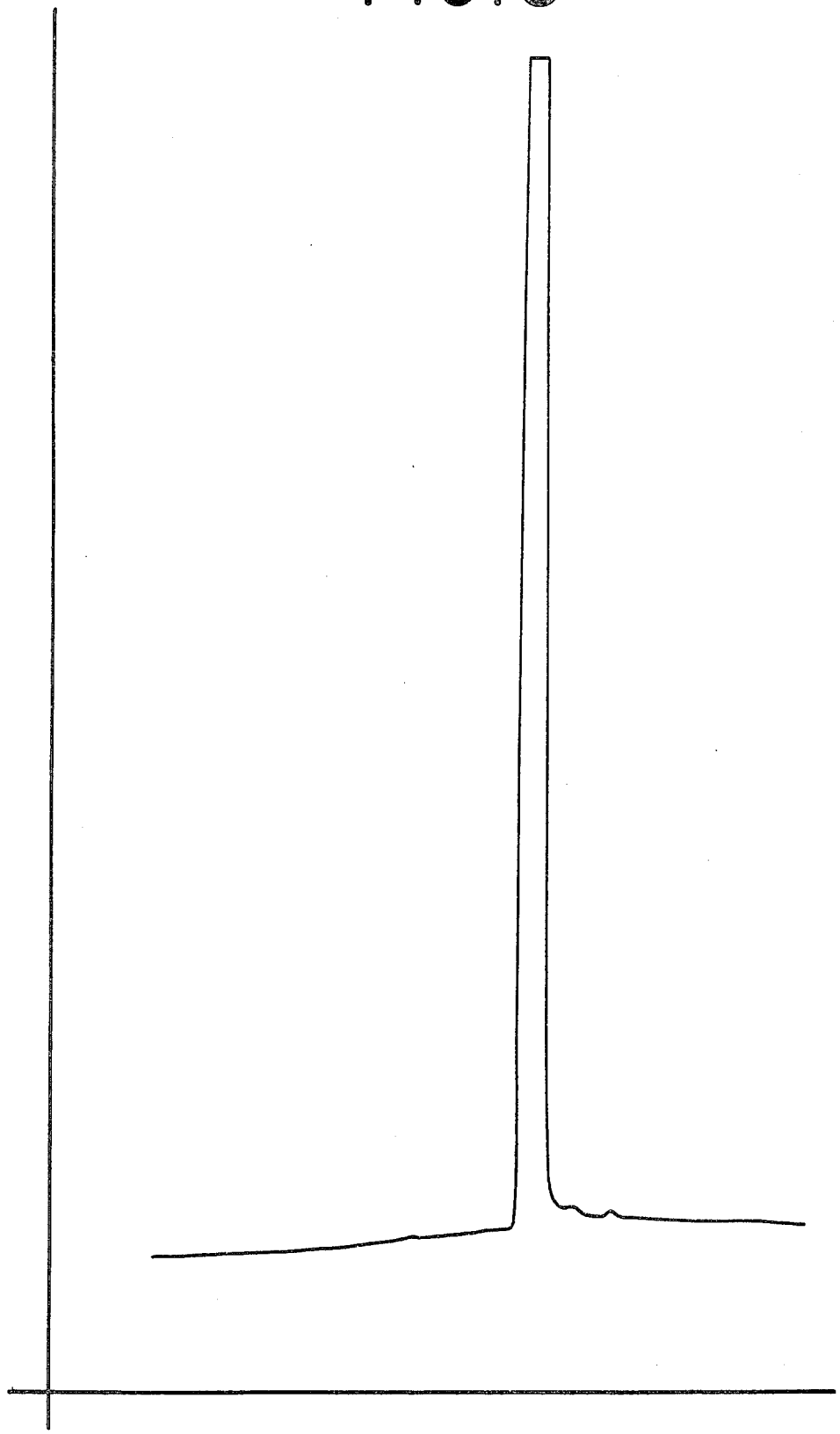
FIG. 8 is the GLC profile for the product produced according to Example III, Fractions 9-12 wherein a Filtrol ® catalyst is used as the dimerizing agent.

FIG. 4 is the GLC profile for Fractions 9–12. FIG. 5 is the infrared spectrum for Fractions 9–12. FIG. 6 is the NMR spectrum for Fractions 9–12. FIG. 7 is the mass spectrum for Fractions 9–12. FIG. 8 is a second GLC profile for Fractions 9–12.

EXAMPLE IV

DIACETYLATION OF ALPHA METHYL STYRENE DIMER

Reaction:

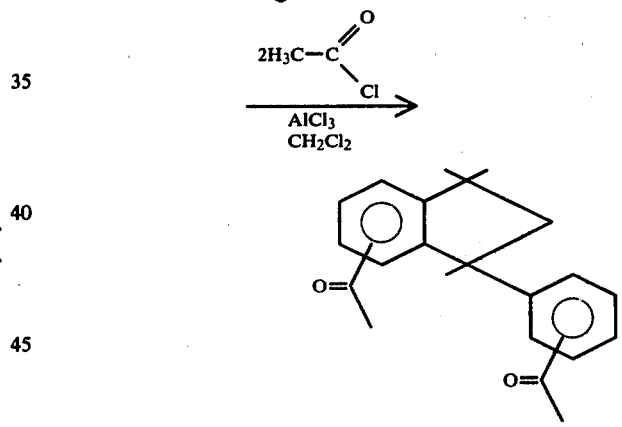

Into a two liter reaction flask equipped with stirrer, thermometer, reflux condenser, "Y" adapter, nitrogen addition tube, addition funnel and two-liter separatory funnel is placed 600 ml CH₂Cl₂ and 238 g of aluminum chloride. Over a fifteen-minute period, 160 g of acetyl chloride is added while maintaining the reaction mass at room temperature. The resulting reaction mass is then cooled to 15°–20° C. and 186 g of alpha methyl styrene dimer prepared according to the process of Example I is added over a three-hour and ten minute period. Much gas evolution is observed. The resulting mixture is stirred at 15°–20° C. for an additional 1.5 hours whereupon the GLC analysis indicates that the reaction has gone to "near" completion.

The resulting reaction mass is then poured into a 4 liter beaker containing 1000 g of chopped ice and 300 g of concentrated hydrochloric acid. The reaction mass is then covered overnight followed by separation of the resulting mixture in a two-liter separatory funnel. The organic layer is washed with two volumes (250 ml each) 10% hydrochloric acid solution and two 250 volumes of water. The resulting mixture is then transferred to a 500 ml distillation flask while stripping CH$_2$Cl$_2$ at atmospheric pressure to a pot temperature of 100° C. The reaction mass is then distilled on a "Y" adapter column yielding the following fractions:

| Fraction | Vapor Temp. | Liquid Temp. | Vac. mm. | Weight of Fraction (gm) |
|---|---|---|---|---|
| 1 | 48/209 | 217/231 | 2.0 | 2.3 |
| 2 | 211 | 233 | 1.9 | 4.4 |
| 3 | 215 | 234 | 1.8 | 18.7 |
| 4 | 215 | 234 | 1.8 | 19.7 |
| 5 | 215 | 234 | 1.9 | 11.5 |
| 6 | 218 | 235 | 2.0 | 20.1 |
| 7 | 218 | 236 | 2.0 | 16.3 |
| 8 | 216 | 236 | 1.8 | 18.7 |
| 9 | 216 | 235 | 1.8 | 21.9 |
| 10 | 216 | 235 | 1.8 | 23.1 |
| 11 | 216 | 236 | 1.8 | 26.6 |
| 12 | 220 | 250 | 2.0 | 27.8 |

The reaction product is then analyzed via GLC (Conditions: 8'×⅛" column, programmed at 80°–250° C. at 8° C. per minute). (Material: OV 101).

FIG. 9 sets forth the GLC profile for the reaction product of this Example IV.

EXAMPLE V

PREPARATION OF MONOACETYLATED ALPHA METHYL STYRENE DIMER

Reaction:

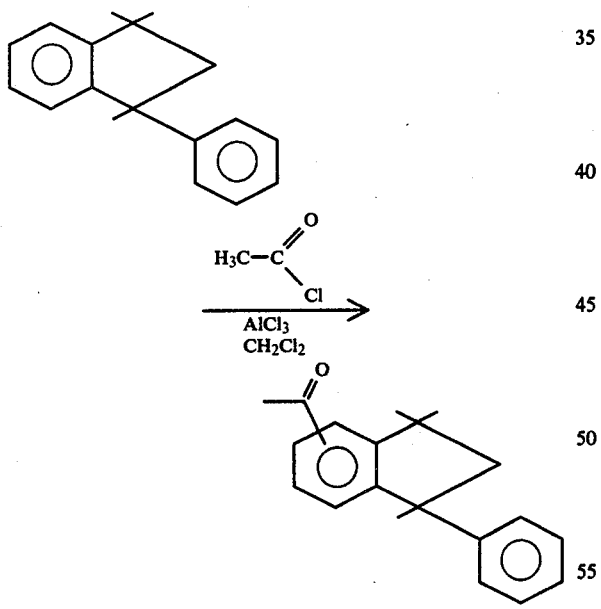

Into a 2,000 ml reaction flask equipped with stirrer, thermometer, condenser, "Y" adapter, addition funnel and nitrogen inlet tube is placed the following materials:

500 ml CH$_2$Cl$_2$
119.0 g AlCl$_3$

At room temperature, 80.0 g of acetyl chloride is added over a fifteen-minute period. This addition is exothermic to less than 30° C. changing the color of the solution from milk white to muddy green. The resulting mixture is then cooled to 3° C. and 186.0 g of alpha methyl styrene dimer prepared according to Example II is added over a two hour and forty-five minute period. This addition causes evolution of much gas. The mixture is stirred at 0° C. for 5.5 hours after addition. The resulting mixture is then poured into a beaker containing 200 g of concentrated hydrochloric acid solution and 750 g of chopped ice and the beaker is covered.

The resulting mixture is then separated in a 2 liter separatory funnel and the organic layer is washed with two 250 ml volumes of 10% hydrochloric acid and two 250 ml volumes of water. The resulting mixture is then transferred to a distillation flask (500 ml) while stripping the CH$_2$Cl$_2$ at atmospheric pressure to a pot temperature of 100° C. The resulting mixture is distilled yielding the following fractions:

| Fraction | Vapor Temp. | Liquid Temp. | Vac. mm. | Weight of Fraction (gm) |
|---|---|---|---|---|
| 1 | 125/127 | 158/158 | 3.0 | 5.5 |
| 2 | 127 | 158 | 3.0 | 5.5 |
| 3 | 128 | 168 | 3.0 | 12.6 |
| 4 | 130 | 178 | 2.9 | 17.0 |
| 5 | 137 | 196 | 2.9 | 14.1 |
| 6 | 155 | 206 | 1.5 | 7.1 |
| 7 | 176 | 216 | 2.0 | 15.9 |
| 8 | 182 | 224 | 2.0 | 13.6 |
| 9 | 185 | 233 | 2.0 | 7.4 |
| 10 | 208 | 238 | 1.7 | 2.8 |
| 11 | 210 | 240 | 1.6 | 8.3 |
| 12 | 212 | 242 | 1.6 | 21.5 |
| 13 | 212 | 243 | 1.6 | 15.9 |
| 14 | 213 | 258 | 1.6 | 19.1 |
| 15 | 209 | 258 | 1.6 | 11.0 |
| 16 | 155 | 271 | 1.6 | 11.4 |

FIG. 10 sets forth the GLC profile for the reaction product of this Example. It will be seen from FIG. 10 that both the monoacylated and diacylated product is obtained. The monacylated and diacylated product may be separated from one another or they may be used in admixture. In the following examples depending upon this Example V, the monoacylated and diacylated products are used in conjunction with one another.

EXAMPLE VI

PREPARATION OF MONOACETYLATED ALPHA METHYL STYRENE DIMER

Reaction:

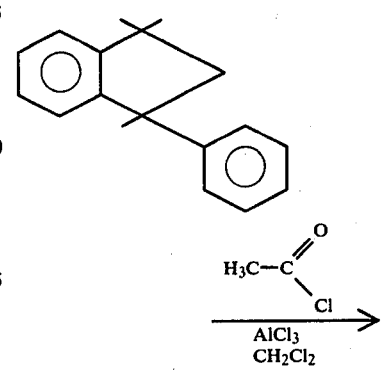

-continued

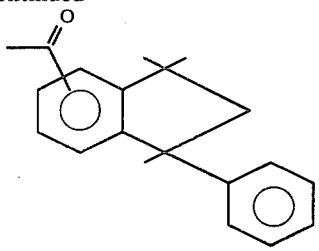

Into a 2,000 ml reaction flask equipped with stirrer, thermometer, condenser, "Y" adapter, addition funnel and nitrogen inlet tube is placed the following materials:

500 ml $CH_2Cl_2$
119.0 g $AlCl_3$

At room temperature, 80.0 g of acetyl chloride is added over a fifteen-minute period. This addition is exothermic to less than 30° C. changing the color of the solution from milk white to muddy green. The resulting mixture in then cooled to 3° C. and 186.0 g of alpha methyl styrene dimerization product produced according to Example III is added over a two hour and forty-five minute period. This addition causes evolution of much gas. The mixture is stirred at 0° C. for 5.5 hours after addition. The resulting mixture is then poured into a beaker containing 200 g of concentrated hydrochloric acid solution and 750 g of chopped ice and the beaker is covered.

The resulting mixture is then separated in a 2 liter separatory funnel and the organic layer is washed with two 250 ml volumes of 10% hydrochloric acid and two 250 ml volumes of water. The resulting mixture is then transferred to a distillation flask (500 ml) while stripping the $CH_2Cl_2$ at atmosperic pressure to a pot temperature of 100° C. The resulting mixture is distilled yielding the following fractions:

| Fraction | Vapor Temp. | Liquid Temp. | Vac. mm. | Weight of Fraction (gm) |
|---|---|---|---|---|
| 1 | 125/127 | 158/158 | 3.0 | 5.5 |
| 2 | 127 | 158 | 3.0 | 5.5 |
| 3 | 128 | 168 | 3.0 | 12.6 |
| 4 | 130 | 178 | 2.9 | 17.0 |
| 5 | 137 | 196 | 2.9 | 14.1 |
| 6 | 155 | 206 | 1.5 | 7.1 |
| 7 | 176 | 216 | 2.0 | 15.9 |
| 8 | 182 | 224 | 2.0 | 13.6 |
| 9 | 185 | 233 | 2.0 | 7.4 |
| 10 | 208 | 238 | 1.7 | 2.8 |
| 11 | 210 | 240 | 1.6 | 8.3 |
| 12 | 212 | 242 | 1.6 | 21.5 |
| 13 | 212 | 243 | 1.6 | 15.9 |
| 14 | 213 | 258 | 1.6 | 19.1 |
| 15 | 209 | 258 | 1.6 | 11.0 |
| 16 | 155 | 271 | 1.6 | 11.4 |

FIG. 10 sets forth the GLC profile for the reaction product of this Example. It will be seen from FIG. 10 that both the monoacylated and diacylated product is obtained. The monoacylated and diacylated product may be separated from one another or they may be used in admixture. In the following examples depending upon this Example VI, the monoacylated and diacylated products are used in conjunction with one another.

EXAMPLE VII

Patchouli oil (80 parts) obtained from the Seychelle Islands is blended with the acylated alpha methyl styrene dimerization product produced according to any one of Examples IV, V or VI (20 parts). The acylated alpha methyl styrene dimerization product is found to act as an extender for the patchouli oil in that the characteristics odor effect of the latter is substantially not modified.

EXAMPLE VIII

The extended patchouli oil prepared according to Example VII is successfully incorporated into a compounded composition of the Chypre type by blending the following ingredients:

| Ingredients | Parts by Weight |
|---|---|
| Cinnamic Aldehyde | 1 |
| Ethyl Methyl Phenyl Glycidate | 1 |
| Methyl Nonyl Acetaldehyde | 2 |
| Oakmoss (Absolute) | 20 |
| Sandalwood Oil (East Indian) | 20 |
| Vetiveryl Acetate | 20 |
| Ylang Oil | 20 |
| Benzoin Resoin (Sumatra) | 30 |
| Alpha Ionone (100%) | 30 |
| Clove Stem Oil (Zanzibar) | 36 |
| Bergamot Oil | 40 |
| Hydroxycitronellal | 40 |
| Iso Eugenol | 50 |
| Extended Patchoiuli Oil (Example VII) | 40 |
| Coumarin | 50 |
| Musk Ketone | 50 |
| Amyl Salicylate | 60 |
| Cedarwood Oil (American) | 60 |
| Citronellol | 60 |
| Benzyl Acetate | 80 |
| Phenyl Ethyl Alcohol | 150 |
| Terpinyl Acetate | 150 |
| TOTAL | 1000 |

A satisfactory chypre perfume containing extended patchouli oil is thus provided.

EXAMPLE IX

A patchouli oil extender base is prepared by blending the following ingredients:

| Ingredients | Parts by Weight |
|---|---|
| Acylated Dimerization Product of Alpha Methyl Styrene (produced according to any one of Examples IV, V or VI) | 38 |
| Galaxolide ® (Registered trademark of International Flavors & Fragrances Inc. identifying a tricyclic isochroman) | 27 |
| Isolongifolene Oxidate | 20 |
| Omega-Hydroxymethyl Longifolene | 10 |
| Cedrol | 3 |
| Sandalwood Oil (East Indian) | 2 |
| TOTAL | 100 |

This mixture (46 parts) is then blended with natural patchouli oil (Seychelles) (60 parts) to provide a satisfactory extended patchouli oil.

EXAMPLE X

The extended patchouli oil prepared in Example IX is incorporated into a compounded perfumery composition of the Fougere type containing the following ingredients:

| Ingredients | Parts by Weight |
|---|---|
| Balsam Peru | 30 |
| Labdanum Resin | 30 |
| Oakmoss Absolute | 30 |
| Sandalwood Oil (East Indian) | 30 |
| Linalyl Acetate | 40 |
| Terpinyl Acetate | 40 |
| Geranium Oil (Bourbon) | 50 |
| Musk Ambrette | 50 |
| Coumarin | 60 |
| Amyl Salicylate | 60 |
| Methyl Ionone | 70 |
| Cedarwood Oil (American) | 80 |
| Clove Stem Oil (Zanzibar) | 80 |
| Vetivert Oil (Bourbon) | 80 |
| Extended Patchouli Oil of Example IX | 130 |
| Lavandin Oil | 140 |
| TOTAL | 1000 |

A satisfactory patchouli perfume containing extended patchouli oil is thusly provided.

What is claimed is:

1. An acylated alpha methyl styrene dimerization product or hydrogenation product thereof having a structure selected from the group consisting of:

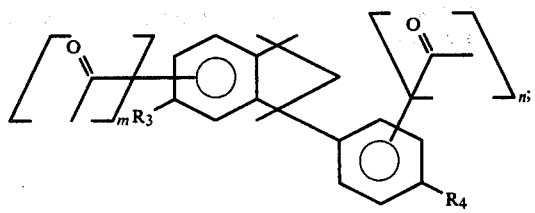

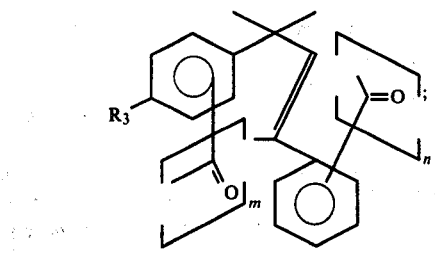

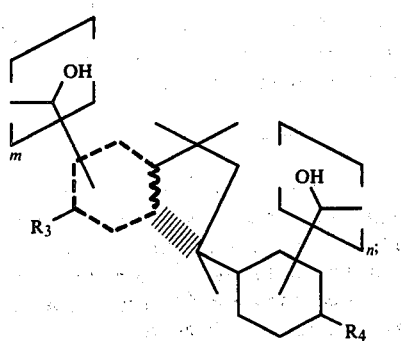

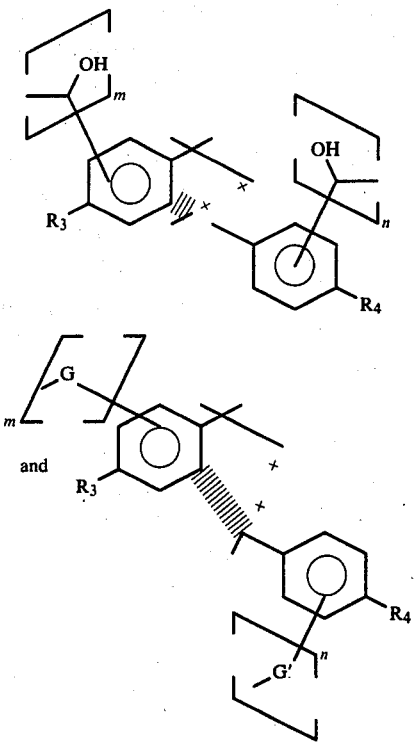

wherein G' and G are each one of the moieties:

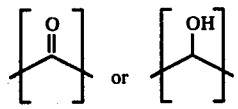

with at least one of G or G' being a moiety having the structure:

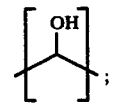

wherein $R_3$ and $R_4$ are the same or different alkyl or hydrogen; wherein the dashed lines and wavy line represent carbon-carbon single bonds or carbon-carbon double bonds with the proviso that when there is one double bond present in the ring having the dashed lines and the wavy line, only the wavy line is a double bond and when there is more than one double bond present in the ring containing the dashed lines and the wavy line, the ring is a benzene ring; and wherein the line ||||||||| represents either a carbon-carbon single bond or no bond; wherein m=0 or 1; and n=0 or 1 and m+n are further defined by the inequality:

$$0 < m+n \leq 2$$

wherein the line +++ represents a carbon-carbon single bond or a carbon-carbon double bond with the proviso that when the line +++ is a carbon-carbon double bond the line ||||||||| is no bond and when the line +++ is a carbon-carbon single bond, the line ||||||||| is a carbon-carbon single bond.

2. A single phase liquid compounded perfumery composition which comprises a natural perfumery oil or synthetic perfumery oil or a mixture of natural perfumery oil and synthetic perfumery oil or a perfumery chemical with which there is intimately admixed from 1 to 30 parts by weight of at least one odorless perfumery extender which is a dimerization product selected from the group consisting of acylated alpha methyl styrene dimerization products, acylated alpha methyl styrene methyl homologue dimerization products, hydrogenated, acylated alpha methyl styrene dimerization products and hydrogenated acylated alpha methyl styrene methyl homologue dimerization products per 100 parts by weight of perfumery oil or perfumery chemical, said acylated alpha methyl styrene dimerization products and said acylated alpha methyl styrene methyl homologue dimerization products having at least one structure selected from the group consisting of:

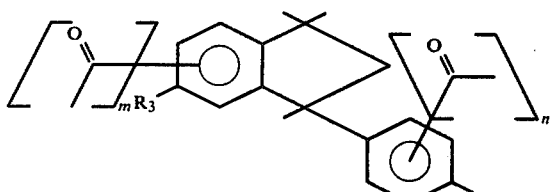

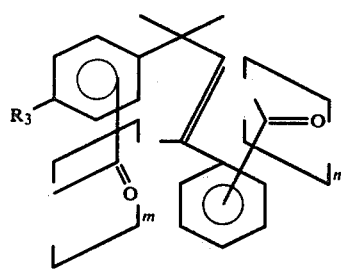

said hydrogenated alpha methyl styrene dimerization products and said hydrogenated alpha methyl styrene homologue dimerization products having at least one structure defined according to a generic structure selected from the group consisting of:

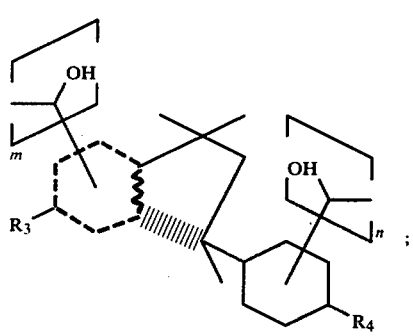

-continued

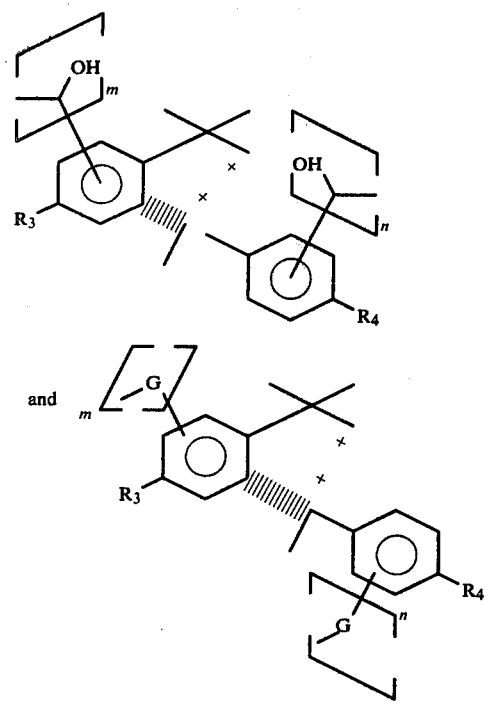

wherein R' and G are each one of the moieties:

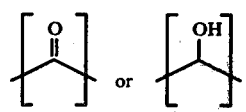

with at least one of G or G' being a moiety having the structure:

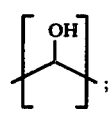

wherein $R_3$ and $R_4$ are the same or different alkyl or hydrogen; wherein the dashed lines and wavy line represent carbon-carbon single bonds or carbon-carbon double bonds with the proviso that when there is one double bond present in the ring having the dashed lines and the wavy line, only the wavy line is a double bond and when there is more than one double bond present in the ring containing the dashed lines and the wavy line, the ring is a benzene ring; and wherein the line ||||||||| represents either a carbon-carbon single bond or no bond; wherein m=0 or 1; and n=0 or 1 and m+n are further defined by the inequality:

$$0 < m+n \leq 2$$

wherein the line +++ represents a carbon-carbon single bond or a carbon-carbon double bond with the proviso that when the line +++ is a carbon-carbon double bond the line ||||||||| is no bond and when the line +++ is a carbon-carbon single bond, the line ||||||||| is a carbon-carbon single bond.

3. The compounded perfumery composition of claim 2 wherein the dimerization product is an alpha methyl styrene dimer having the structure:

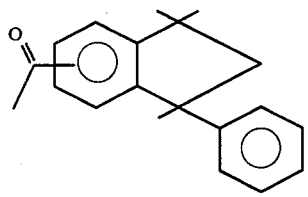

4. The compounded perfumery composition of claim 2 wherein the acylated dimerization product is a hydrogenated acylated dimerization product having at least one structure selected from the group consisting of:

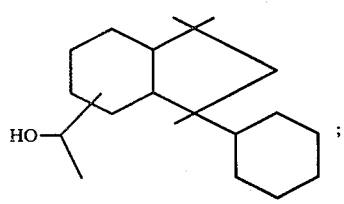

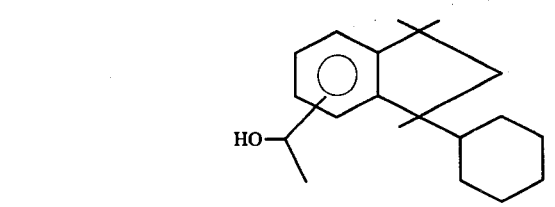

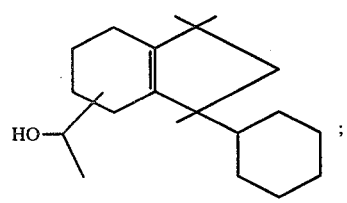

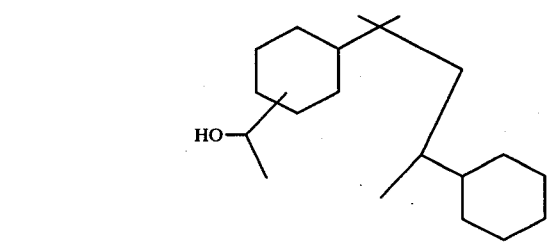

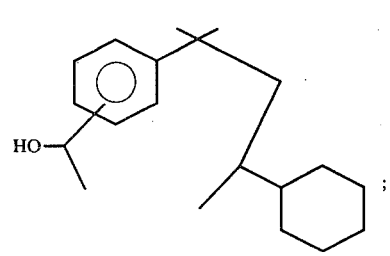

-continued

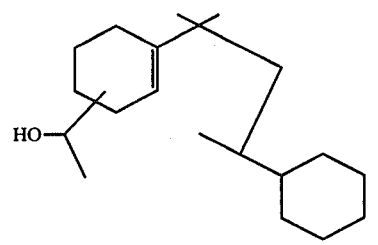

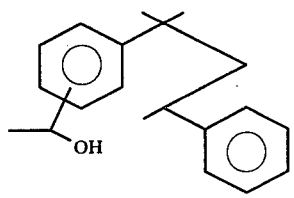

and

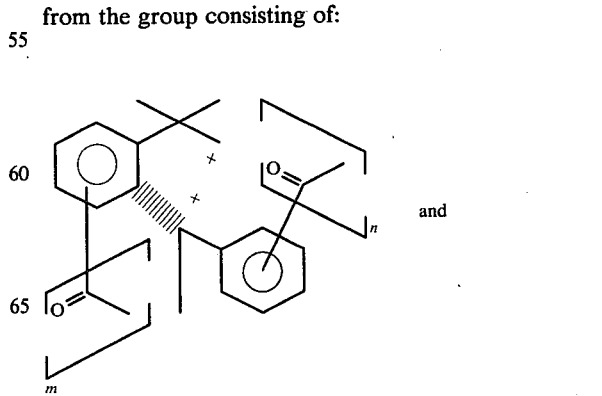

5. A process for the dilution of a natural perfumery or a synthetic perfumery oil or a mixture of natural perfumery oil and synthetic perfumery oil or a perfumery chemical without substantially diminishing the aroma strength of said natural perfumery oil, synthetic perfumery oil, mixture of natural perfumery oil and synthetic perfumery oil or perfumery chemicals, comprising the step of intimately admixing about 100 parts by weight of said natural perfumery oil, synthetic perfumery oil, mixture of natural perfumery oil and synthetic perfumery oil or perfumery chemicals with from about 1 up to about 3 parts by weight of an odorless perfumery extender which is one or more dimerization products selected from the group consisting of acylated alpha methyl styrene dimerization products, and hydrogenated acylated alpha methyl styrene dimerization products, said acylated alpha methyl styrene dimerization products being defined by at least one generic structure selected from the group consisting of:

-continued

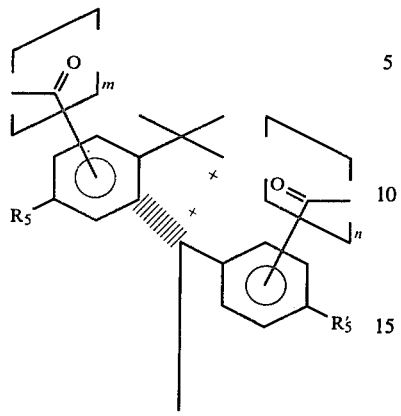

wherein one of $R_5$ and $R_5'$ is methyl and the other of $R_5$ and $R_5'$ is hydrogen or $R_5$ and $R_5'$ are both methyl; wherein the line, ∥∥∥∥∥ represents a carbon-carbon single bond or no bond and wherein the line ++++ represents a carbon-carbon single bond or a carbon-carbon double bond, with the proviso that when the line +++ is a carbon-carbon double bond then the line ∥∥∥∥∥ is no bond and when the line ++++ is a carbon-carbon single bond then the line ∥∥∥∥∥ is a carbon-carbon single bond, and said hydrogenated acylated alpha methyl styrene dimerization product having at least one structure defined according to at least one of the generic structures selected from the group consisting of:

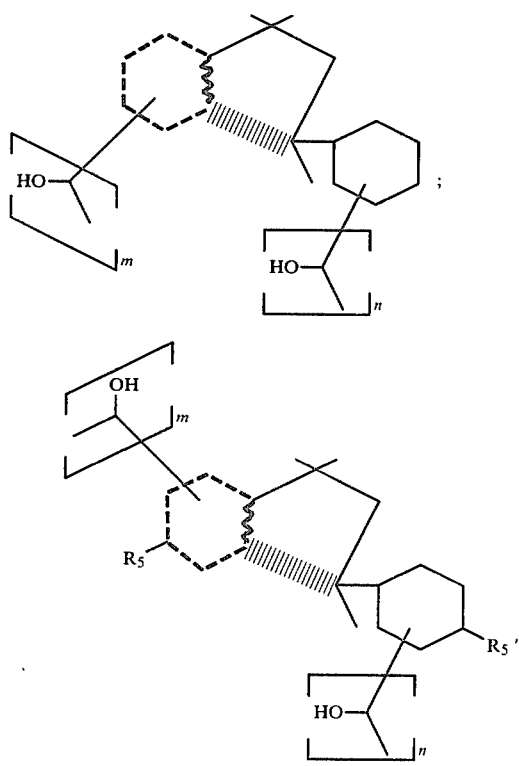

-continued

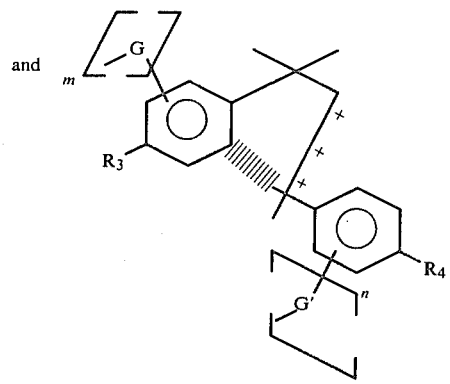

wherein one of $R_5$ and $R_5'$ is methyl and the other is hydrogen or each of $R_5$ and $R_5'$ is methyl; wherein the dashed lines and the wavy line represent carbon-carbon single bonds or no carbon-carbon double bonds with the proviso that when there is one double bond present in the ring having a wavy line and dashed lines, only the wavy is a double bond and when there is more than one double bond present in the ring containing the dashed lines and the wavy line, the ring containing the dashed lines and the wavy line is a benzene ring; and wherein the line ∥∥∥∥∥ represents either a carbon-carbon single bond or no bond and wherein G and G' represents one of the moieties:

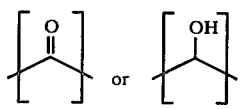

with at least one of G and G' being a moiety having the structure:

6. The process of claim 5 wherein the dimerization product is an acylated alpha methyl stryene dimerization product defined according to the structure:

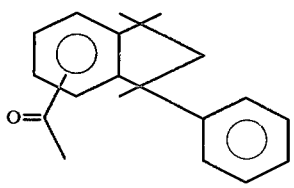

7. The process of claim 5 wherein the dimerization product is a hydrogenated acylated dimerization product of alpha methyl styrene having a structure selected from the group consisting of:

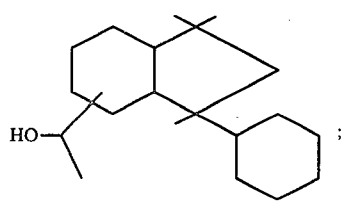;
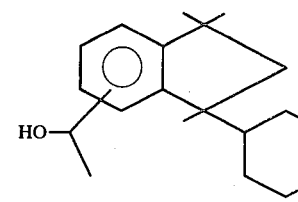;
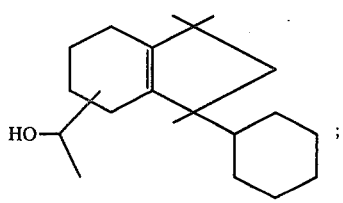;
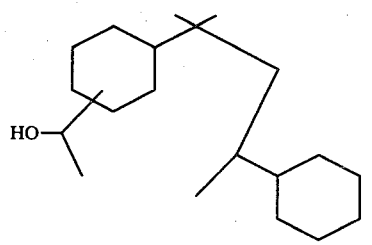;
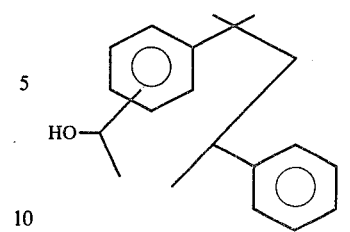;
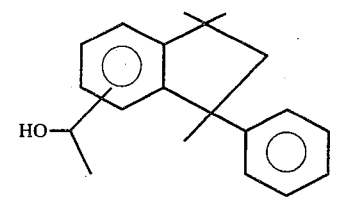;
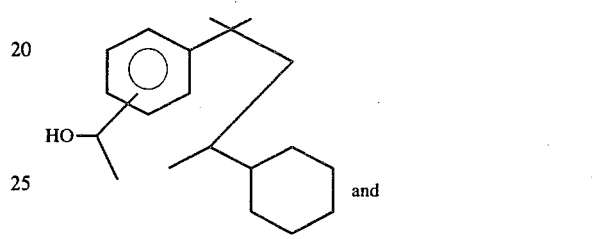 and
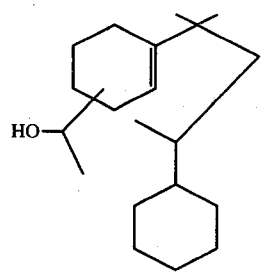
* * * * *